(12) United States Patent
Kim et al.

(10) Patent No.: US 9,603,789 B2
(45) Date of Patent: Mar. 28, 2017

(54) COMPOSITION CONTAINING A NATURAL EXTRACT

(75) Inventors: Jeong-Hwan Kim, Paju-si (KR); Won Seok Park, Seou (KR); Hyun Ju Koh, Anyang-si (KR); Hong-Ju Shin, Seongnam-si (KR); Do-Hoon Kim, Yongin-si (KR); Jong Hee Park, Yongin-si (KR); Chang-Geun Yi, Yongin-si (KR); Hyoung Jun Kim, Yongin-si (KR); Jung A Seo, Daegu (KR)

(73) Assignee: AMOREPACIFIC CORPORATION (KR)

( * ) Notice: Subject to any disclaimer, the term of this patent is extended or adjusted under 35 U.S.C. 154(b) by 430 days.

(21) Appl. No.: 13/390,232

(22) PCT Filed: Aug. 13, 2010

(86) PCT No.: PCT/KR2010/005342
§ 371 (c)(1),
(2), (4) Date: Feb. 13, 2012

(87) PCT Pub. No.: WO2011/019239
PCT Pub. Date: Feb. 17, 2011

(65) Prior Publication Data
US 2012/0141613 A1    Jun. 7, 2012

(30) Foreign Application Priority Data

| Aug. 14, 2009 | (KR) | 10-2009-0075082 |
| Aug. 14, 2009 | (KR) | 10-2009-0075083 |
| Aug. 14, 2009 | (KR) | 10-2009-0075084 |
| Aug. 14, 2009 | (KR) | 10-2009-0075085 |
| Aug. 14, 2009 | (KR) | 10-2009-0075219 |
| Aug. 14, 2009 | (KR) | 10-2009-0075242 |
| Aug. 14, 2009 | (KR) | 10-2009-0075280 |

(51) Int. Cl.

| A61K 36/00 | (2006.01) |
| A61K 8/97 | (2017.01) |
| A61K 36/254 | (2006.01) |
| A61K 36/481 | (2006.01) |
| A61K 36/484 | (2006.01) |
| A61K 36/708 | (2006.01) |
| A61K 36/73 | (2006.01) |
| A61K 36/756 | (2006.01) |
| A61K 36/78 | (2006.01) |
| A61Q 19/00 | (2006.01) |
| A61Q 19/02 | (2006.01) |

(52) U.S. Cl.
CPC .............. *A61K 8/97* (2013.01); *A61K 36/254* (2013.01); *A61K 36/481* (2013.01); *A61K 36/484* (2013.01); *A61K 36/708* (2013.01); *A61K 36/73* (2013.01); *A61K 36/756* (2013.01); *A61K 36/78* (2013.01); *A61Q 19/00* (2013.01); *A61Q 19/02* (2013.01)

(58) Field of Classification Search
None
See application file for complete search history.

(56) References Cited

U.S. PATENT DOCUMENTS

| 6,447,820 B1 * | 9/2002 | Niazi |
| 2006/0292108 A1 | 12/2006 | Hanna et al. |

FOREIGN PATENT DOCUMENTS

| CN | 1335123 A | * | 2/2002 |
| CN | 1443056 A | | 9/2003 |
| CN | 1857196 A | * | 11/2006 |
| CN | 1857513 A | * | 11/2006 |
| CN | 101028238 A | * | 9/2007 |
| CN | 101040971 A | | 9/2007 |
| CN | 101066305 A | | 11/2007 |
| CN | 101080215 A | | 11/2007 |
| CN | 101229115 A | | 7/2008 |
| CN | 101390818 A | | 3/2009 |
| CN | 101444468 A | | 6/2009 |
| JP | 02233795 A | * | 9/1990 |
| JP | 03-093710 A | | 4/1991 |
| JP | 3-188008 A | | 8/1991 |
| JP | 05-097653 A | | 4/1993 |
| JP | 07010738 A | * | 1/1995 |
| JP | 11-100324 A | | 4/1999 |
| JP | 2001-031555 A | | 2/2001 |
| JP | 2001048801 A | * | 2/2001 |
| JP | 2001064192 A | * | 3/2001 |
| JP | 2001-97842 A | | 4/2001 |
| JP | 2002-145752 | | 5/2002 |
| JP | 2002234828 A | * | 8/2002 |

(Continued)

OTHER PUBLICATIONS

International Search Report for corresponding International Application No. PCT/KR2010/005342 (Form PCT/ISA/210).

(Continued)

*Primary Examiner* — Qiuwen Mi
(74) *Attorney, Agent, or Firm* — Merchant & Gould P.C.

(57) ABSTRACT

Disclosed is a composition containing an active ingredient or ingredients comprising an extract or extracts of one or more constituents selected from the group consisting of *Astragalus membranaceus, Saururus chinensis, Glycyrrhizae radix*, rose, rhubarb, *Acanthopanax senticosus* and cortex *Phellodendri*. The composition is efficacious in suppressing acneiform pigment deposition and/or pitted scars, and can be used to advantage in various ways in the fields of cosmetics, foods and drugs.

7 Claims, 31 Drawing Sheets

(56) References Cited

FOREIGN PATENT DOCUMENTS

| | | |
|---|---|---|
| JP | 2003-26592 A | 1/2003 |
| JP | 2003-38140 A | 2/2003 |
| JP | 2003-238379 A | 8/2003 |
| JP | 2004-10505 | 1/2004 |
| JP | 2004-43358 A | 2/2004 |
| JP | 2004-161623 A | 6/2004 |
| JP | 2005-8572 A | 1/2005 |
| KR | 10-1999-0053083 A | 7/1999 |
| KR | 10-0284120 B1 | 12/2000 |
| KR | 10-2002-0035656 A | 5/2002 |
| KR | 10-2002-0084877 A | 11/2002 |
| KR | 10-2003-0005093 A | 1/2003 |
| KR | 10-2004-0061733 A | 7/2004 |
| KR | 2004058851 A * | 7/2004 |
| KR | 10-2004-0075135 A | 8/2004 |
| KR | 10-2005-0004354 A | 1/2005 |
| KR | 20050002581 A * | 1/2005 |
| KR | WO 2005000262 A1 * | 1/2005 ............ A61K 8/97 |
| KR | 10-0530669 B1 | 11/2005 |
| KR | 10-2006-0101100 A | 9/2006 |
| KR | 10-2006-0111026 A | 10/2006 |
| KR | 10-2008-0006568 A1 | 1/2008 |
| KR | 10-0844516 B1 | 7/2008 |
| WO | WO 0205757 A1 * | 1/2002 |
| WO | WO 2006/105450 A2 | 10/2006 |
| WO | WO 2006/109898 | 10/2006 |

OTHER PUBLICATIONS

Office Action from Chinese Application No. 201080046468.4 mailed Nov. 28, 2012.
Yun et al., "A Study on the Using of the Natural Plant Extracts for Acne Skin Care" (Feb. 28, 2006). Abstract.
Lee et al., "Isolation of Melanin Biosynthesis Inhibitory Compounds from the Phellodendri Cortex", *Kor. J. Pharmacogn*, 38(4): 387-393 (2007). Abstract.
Office Action for Korean Patent Application No. 10-2009-0075082 (mailed Jun. 24, 2014).
Office Action for Korean Patent Application No. 10-2009-0075085 (mailed Jun. 24, 2014).
Office Action for Korean Patent Application No. 10-2009-0075280 (mailed Jun. 24, 2014).
Office Action for Japanese Patent Application No. 2012-524652 (mailed Jul. 29, 2014).
Office Action for Korean Patent Application No. 10-2009-0075085 (mailed Oct. 30, 2014).
Office Action for Chinese Patent Application No. 201310576546.7 (mailed Sep. 28, 2014).
"Home-made pack book" Hwangjo Corporation, China spinning and weaving publishing house (Jul. 2008) p. 201.
Office Action for Korean Patent Application No. 10-2009-0075219 (mailed Dec. 5, 2014).
Wook et al. "Inhibition of Matrix Metalloproteinase by Flavonoids," *MPPS*, pp. 1-56 (2007).
Seo et al., "Large-scale and effective screening of Korean medicinal plants for inhibitory activity on matrix metalloproteinase-9," *J. Ethnopharmacol*, (97)1:101-06 (2005).
Office Action for Korean Patent Application No. 10-2009-0075219 (mailed Dec. 28, 2014).
Office Action for Korean Patent Application No. 10-2009-0075082 (mailed Dec. 28, 2014).
Office Action for Chinese Patent Application No. 201410122436.8 (mailed Feb. 17, 2015).
Lingqian Kong: "Coarse Cereals for Health Preservation", The Chinese Overseas Publishing House, p. 166, First version in Jan. 2007.
Office Action for Chinese Patent Application No. 201410122476.2 (mailed Apr. 3, 2015).
Office Action for Korean Patent Application No. 10-2015-0016694 (mailed Apr. 17, 2015).
Ruanxiwen, "Early stage observation regarding to rhubarb medical soap treat against dermatitis seborrheic and acne", *Fujian Drug Journal*, vol. 12 (1st ed.), pp. 61-62 (1990).
Koichi, "The research about skin-whitening effect of herb medicine: Tyrosinase activity inhibition ingredient of rhubarb", *A separate volume of Oriental Medicine of the Japanese Overseas Medicine*, vol. 18 (6th ed.), p. 49 (1996).
Office Action for Korean Patent Application No. 10-2009-0075219 (mailed Jun. 25, 2015).
Office Action for Chinese Patent Application No. 201410122420.7 (mailed Jul. 1, 2015).
Office Action for Korean Patent Application No. 10-2009-0075084 (mailed Jul. 6, 2015).
Office Action for Korean Patent Application No. 10-2009-0075082 (mailed Jul. 27, 2015).
Huwipang Chen, "Melanin Synthesis Inhibitor consist of plant extracts comprising Ginko, Acanthopanax senticosus, Gentiana scabra Bunge and etc.," Foreign herbal medicine • Volume, Fifth version, vol. 22, Jan. 2007, p. 255.
Newswire, Mar. 4, 2007, available at: http://www.newswire.co.kr/newsRead.php?no=230886&ected.
Office Action from Korean Patent Application No. 10-2015-0016694 (mailed Oct. 27, 2015).
Office Action from Chinese Patent Application No. 201410122436.8 (mailed Nov. 2, 2015).
Newspaper, The Dong-A Ilbo, p. 40 (May 28, 1999).
Wang et al., "Effect of Acne Drink on Cortical Secretion Rate of an Acne Vulgaris Patient", *Fujian Traditional Chinese Medicine*, 35(4):7-8 (Aug. 2004).
Morrison, "The Sweet Life of an Aromamic Lady", *The Press of Shantou University*, 2nd ed., p. 108 (Jun. 2008).
Liu, "Cosmetology in Traditional Chinese Medicine", *The China Traditional Medicine Press*, 1st ed., p. 67 (Nov. 2006).

\* cited by examiner

COMPOSITION CONTAINING A NATURAL EXTRACT

This application is a U.S. National Stage Application under 35 U.S.C. §371 of International Patent Application No. PCT/KR2010/005342, filed 13 Aug. 2010, which claims the benefit of priority to: Korean Patent Application No. 10-2009-0075082, filed 14 Aug. 2009; Korean Patent Application No. 10-2009-0075083, filed 14 Aug. 2009; Korean Patent Application No. 10-2009-0075084, filed 14 Aug. 2009; Korean Patent Application No. 10-2009-0075085, filed 14 Aug. 2009; Korean Patent Application No. 10-2009-0075219, filed 14 Aug. 2009; Korean Patent Application No. 10-2009-0075242, filed 14 Aug. 2009; and Korean Patent Application No. 10-2009-0075280, filed 14 Aug. 2009, the disclosures of all of which are hereby incorporated by reference in their entireties. The International Application was published in Korean on 17 Feb. 2011 as WO 2011/019239. To the extent appropriate, a claim of priority is made to each of the above disclosed applications.

TECHNICAL FIELD

The present disclosure relates to a composition containing one or more extracts selected from the group consisting of *Astragalus membranaceus*, *Saururus chinensis*, *Glycyrrhizae radix*, rose, rhubarb, *Acanthopanax senticosus* and *Phellodendri* cortex as active ingredients.

BACKGROUND

In general, acne is caused by increased sebum production owing to increased androgen production. Specifically, sebum production by androgen and hyperkeratinization of follicles result in narrowing or and, in severe cases, blocking the follicles. When the follicle is narrowed or blocked, sebum cannot be excreted from the follicle, creating microcomedones. In these conditions, the anaerobic bacterium *Propionibacterium acnes* growing in the follicle may cause inflammation.

As a result of the inflammation, erythema, itching or swelling occurs and, in severe cases, hyperpigmentation may occur. If the acne is squeezed or pressed, the inflammation may aggravate as the comedone bursts. Also, it is highly likely that acne scar develops as a result of tissue damage.

The inflammatory acne may be induced by various causes. For example, various additives included in cosmetics may cause inflammatory acne when they remain on the skin. Also, sebum excreted from the body, sweat, UV, etc. may cause skin inflammations.

Currently, researches are focused only on the treatment of the inflammation caused by the inflammatory acne. However, even after the inflammation is treated, erythema or scar may remain and cause negative effects in appearance. Thus, the inventors of the present disclosure performed researches to suppress or prevent pigmentation and scarring caused by inflammatory acne.

SUMMARY OF THE INVENTION

Technical Problem

The present disclosure is directed to providing a composition for suppressing acnegenic pigmentation.

The present disclosure is also directed to providing a composition for suppressing acne scars.

The present disclosure is also directed to providing an aftercare composition for aftereffect of acne.

Technical Solution

In one general aspect, the present disclosure provides a composition containing one or more extracts selected from the group consisting of *Astragalus membranaceus*, *Saururus chinensis*, *Glycyrrhizae radix*, rose, rhubarb, *Acanthopanax senticosus* and *Phellodendri* cortex as active ingredients.

Advantageous Effects

The composition according to the present disclosure is effective in suppressing acnegenic pigmentation and/or scars.

DETAILED DESCRIPTION

Figure 1:
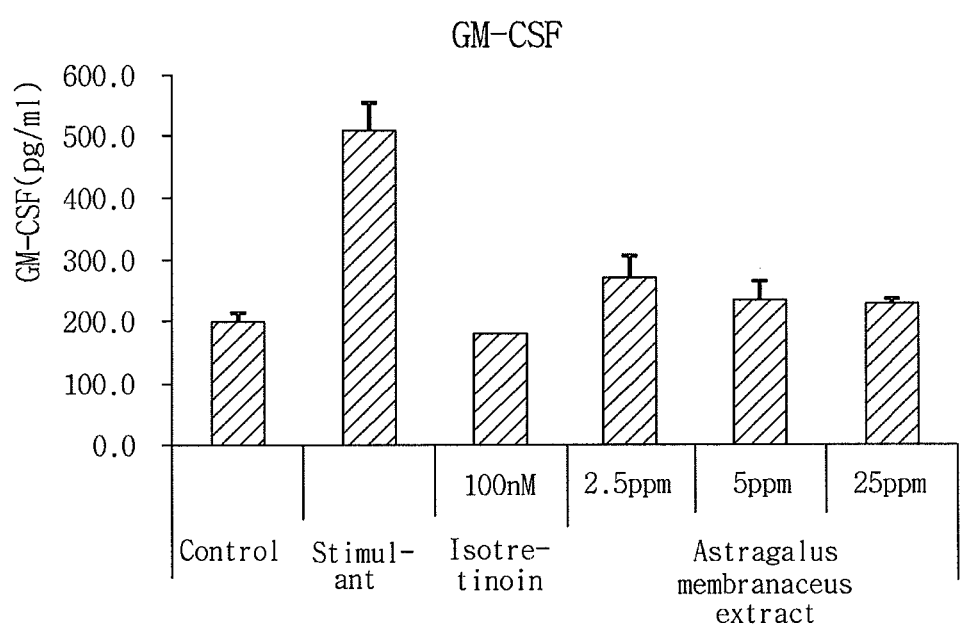
FIGS. 1-4 show inflammatory cytokine inhibiting effect of an *Astragalus membranaceus* extract for GM-CSF (FIG. 1), IL-1α (FIG. 2), IL-8 (FIG. 3) and TNF-α (FIG. 4)

The composition according to the present disclosure contains one or more extracts selected from the group consisting of *Astragalus membranaceus, Saururus chinensis, Glycyrrhizae radix*, rose, rhubarb, *Acanthopanax senticosus* and *Phellodendri* cortex as active ingredients. The composition containing one or more extracts selected from the group consisting of *Astragalus membranaceus, Saururus chinensis, Glycyrrhizae radix*, rose, rhubarb, *Acanthopanax senticosus* and *Phellodendri* cortex has an effect of inhibiting and suppressing acnegenic pigmentation and/or acne scars. In an exemplary embodiment, the composition according to the present disclosure is a composition for suppressing acnegenic pigmentation containing one or more extracts selected from the group consisting of *Astragalus membranaceus, Saururus chinensis, Glycyrrhizae radix*, rose, rhubarb, *Acanthopanax senticosus* and *Phellodendri* cortex as active ingredients. In another exemplary embodiment, the composition according to the present disclosure is a composition for suppressing acne scars containing one or more extracts selected from the group consisting of *Astragalus membranaceus, Saururus chinensis* and *Glycyrrhizae radix* as active ingredients.

*Astragalus membranaceus* is a dicotyledonous perennial grass belonging to the family Fabaceae, order Fabales. It grows between rocks in mountains, is about 40-70 cm tall, and is distributed in Korea, Japan, Northeast China, Eastern Siberia, and so forth. In the Oriental medicine, the plant is harvested in autumn and used after removing the head and root hairs followed by drying in the sunlight.

*Saururus chinensis* is a dicotyledonous perennial grass belonging to the family Saururus, order Piperales. The white rhizome grows transversely in the mud. It is 50-100 cm tall and blossoms in June to August. The plant grows mainly on damp ground, and its Chinese name meaning "three white grass" is derived because its root, leaves and flowers are white. It is known to be efficacious against beriberi, jaundice, hepatitis, or the like, and is distributed in Korea, Japan and China.

*Glycyrrhizae radix* (*Glycyrrhiza uralensis*) is a dicotyledonous herb belonging to the family Fabaceae and is widely used as medicinal plants. In addition to Korea, it is distributed in Northeast China, Siberia and Mongolia. The angular stem is straight and grows about 1 m tall. The leaves are alternate and imparipinnately compound. The purple flowers bloom in July to August, and are 1.4-2.5 cm long. The reddish brown root grows deep into the ground, tastes sweet, and is used as sweetening or medicinal herb.

Rose (*Rosa* spp.) collectively refers to dicotyledonous plants belonging to the family Rosaceae, order Rosales, both wild and cultivated. Rose is a flowering shrub, cultivated for its beauty fragrance. A variety of species are widely cultivated from the arctic to the subarctic, temperate and subtropical zones of the northern hemisphere.

Rhubarb (*Rheum undulatum*) refers to perennial grasses belonging to the family Polygonaceae, order Caryophyllales. Rhubarb grows mainly on damp ground in valleys and is native to China. It has thick yellow root and the straight stem grows as high as 1 m. Its taproot is mainly used as medicine. The taproot is cut and dried for medicinal use either after removing the bark and fine roots or as it is. It is used as an anti-inflammatory purgative and for many other purposes.

*Acanthopanax senticosus* is a deciduous shrub of the family Araliaceae. It is about 2-3 m tall. *Acanthopanax senticosus* has long and thin thorns and has palm-shaped alternate compound leaves. In the generic name *Acanthopanax*, the prefix acantho-means 'thorny' and *Panax* means 'all-heal'. That is, the generic name means 'all-healing horny plant'. From long ago, the plant has been widely to treat neuralgia, arthritis, hypertension, neurasthenia and diabetes and as a tonic.

*Phellodendri* cortex refers to the bark of *Phellodendron amurense* used as medicine. *Phellodendron amurense* is a deciduous broadleaf tree of the family Rutaceae. It grows about 10 m tall. The bark is rich in cork and the inner bark is yellow. *Phellodendri* cortex is obtained by peeling the bark around the summer solstice and drying in the sunlight after chopping. *Phellodendri* cortex is known to reduce blood sugar, inhibit growth of *Pneumococcus, Mycobacterium tuberculosis, Staphylococcus*, etc., inhibit proliferation of tumor cells, and has sterilizing effect. *Phellodendri* cortex is also known to promote secretion of gastric juice via palate reflex and improve appetite.

The extract may be obtained according to commonly employed methods, without particular limitation. In an exemplary embodiment, the extract of one or more selected from the group consisting of *Astragalus membranaceus, Saururus chinensis, Glycyrrhizae radix*, rose, rhubarb, *Acanthopanax senticosus* and *Phellodendri* cortex may be extracted using distilled water or an organic solvent such as $C_1$-$C_5$ anhydrous or hydrous low alcohol. In another exemplary embodiment, the extract may be obtained by hot water extraction. The extraction efficiency of the hot water extraction may be improved by setting vacuum and high-pressure conditions.

In another exemplary embodiment, the extract of one or more selected from the group consisting of *Astragalus membranaceus, Saururus chinensis* and *Glycyrrhizae radix* has an effect of inhibiting gelatinase. Gelatinase is a proteolytic enzyme expressed in various molds or yeasts that allows for liquefaction of gelatin. The kind of the gelatinase is not particularly limited. The gelatinases that are expressed in humans include matrix metalloproteinase-9 (MMP-9) and matrix metalloproteinase-2 (MMP-2). In another exemplary embodiment, the extract of one or more selected from the group consisting of *Astragalus membranaceus, Saururus chinensis* and *Glycyrrhizae radix* has an effect of inhibiting MMP-9 and/or MMP-2. The composition according to the present disclosure suppresses and prevents acne scars by inhibiting gelatinase, specifically MMP-9 and/or MMP-2.

The composition according to the present disclosure may be used in various applications without particular limitation. For example, it may be prepared into formulations for external skin application, specifically cosmetics, or pharmaceutical compositions.

The composition for external skin application according to the present disclosure may be in the form of a solution in an oily or aqueous medium, a suspension, an emulsion, or a dry powder that can be dissolved in sterilized water before use. A water-in-oil emulsion may be prepared by emulsifying the active ingredient in an oil phase such as a vegetable oil like olive oil or a mineral oil like liquid paraffin using a naturally occurring phospholipid such as soybean lecithin, an anhydrous hexitol such as sorbitan monooleate, a fatty acid-derived ester, or a condensation product of an anhydrous hexitol- and fatty acid-derived ester with ethylene oxide such as polyoxyethylene sorbitol monooleate as an emulsifier.

In an exemplary embodiment, the composition according to the present disclosure for external skin application may comprise the extract of *Astragalus membranaceus, Saururus chinensis, Glycyrrhizae radix*, rose, rhubarb, *Acanthopanax senticosus* or *Phellodendri* cortex in an amount of 0.1-20 wt %, more specifically 0.5-20 wt %, based on the total weight of the composition. When the content of the extract is too small, the effect of managing and improving skin condition is only slight. And, when the content of the extract is too large, the efficiency of adding the extract is decreased and stability problem may occur.

The present disclosure also provides a cosmetic composition comprising the composition. When the composition is formulated into a cosmetic composition, it may be used to suppress or improve acnegenic pigmentation. Also, it may be used to suppress or improve acne scarring. The cosmetic composition may be in any form without particular limitation. For example, the cosmetic composition may be in the form of emollient lotion, nourishing lotion, massage cream, nourishing cream, pack, gel, or skin adhesive type cosmetic. Also, it may be in the form of formulation for transdermal administration such as lotion, ointment, gel, cream, patch or spray. Those skilled in the art may easily add other ingredients considering the type or purpose of each formulation or cosmetic composition.

The present disclosure further provides a pharmaceutical composition comprising the composition. The pharmaceutical composition comprising the composition according to the present disclosure may be a composition for improving and suppressing acnegenic pigmentation and/or acne scars.

When the composition according to the present disclosure is used as medicine, an organic or inorganic carrier may be added to the composition as the active ingredient to prepare a solid, semisolid or liquid type formulation for oral or parenteral administration.

The formulation for oral administration may be tablet, pill, granule, hard or soft capsule, powder, fine powder, dust, emulsion, syrup, pellet, or the like. And, the formulation for parenteral administration may be injection, drip, ointment, lotion, spray, suspension, emulsion, suppository, or the like. The formulation may be prepared easily according to commonly employed methods and surfactant, excipient, colorant, fragrance, preservative, stabilizer, buffer, suspending agent or other commonly used adjuvants may be used appropriately.

The pharmaceutical composition according to the present disclosure may be administered orally, rectally, topically, transdermally, intravenously, intramuscularly, intraabdominally or subcutaneously.

And, the administration dosage of the active ingredient will vary depending on the age, sex and body weight of the subject to be treated, the specific disease or physiological condition to be treated, the severity of the disease or physiological condition, the route of administration, and the discretion of a diagnoser. The determination of the administration dosage based on these factors is within the level of those skilled in the art. A general administration dosage is 0.001-2000 mg/kg/day, more specifically 0.5-1500 mg/kg/day.

The present disclosure also provides an aftercare composition containing an active ingredient or ingredients comprising an extract or extracts of one or more constituents selected from the group consisting of *Astragalus membranaceus, Saururus chinensis, Glycyrrhizae radix*, rose, rhubarb, *Acanthopanax senticosus* and *Phellodendri* cortex. More specifically, the present disclosure also provides an aftercare composition for systematically treating aftereffect of acne such as pigmentation and/or scars and managing and improving skin condition.

In an exemplary embodiment, the aftercare composition according to the present disclosure may comprise the extract of *Astragalus membranaceus, Saururus chinensis, Glycyrrhizae radix*, rose, rhubarb, *Acanthopanax senticosus* or *Phellodendri* cortex in an amount of 0.1-20 wt %, more specifically 0.5-20 wt %, based on the total weight of the composition. When the content of the extract is too small, the effect of managing and improving skin condition is only slight. And, when the content of the extract is too large, the efficiency of adding the extract is decreased and stability problem may occur.

As used herein, the term 'aftercare' refers to a systematic post-management for managing and improving skin condition. For example, after vacation at the riverside, beach or valley or after long hours of tanning, inflammation may occur as the skin is excessively exposed to UV. Also, various additives included in sun cream, oil, or the like may induce inflammatory acne when they remain on the skin. In addition, skin troubles including inflammatory acne may be caused by various causes in daily lives. The aftercare collectively refers to the post-management for managing and improving skin condition against the skin troubles including inflammatory acne. And, the aftercare composition may be a composition that is adhered, deposited or applied on the skin for aftercare.

The present disclosure further provides a food additive, functional food or health food composition comprising the composition. Specifically, the composition may be a composition for improving and suppressing acnegenic pigmentation and/or scars.

The composition according to the present disclosure may be a food additive or functional food composition of various forms. It may be processed into fermented milk, cheese, yogurt, juice, probiotic, dietary supplement, and various food additives.

In an exemplary embodiment, the composition may comprise other ingredients that can provide a synergic effect as long as they do not negatively affect the effect desired in the present disclosure. For example, fragrance, pigment, sterilizer, antioxidant, antiseptic, moisturizer, thickener, mineral, emulsifier, synthetic polymer material, etc. may be further included for improvement of physical properties. In addition, auxiliary ingredients such as water-soluble vitamin, oil-soluble vitamin, polypeptide, polysaccharide, seaweed extract, or the like may be further included. Those skilled in the art will select these ingredients without difficulty and the addition amount may be selected within the range not negatively affecting the effect desired in the present disclosure.

The composition according to the present disclosure may be in various forms, including solution, emulsion, viscous mixture, tablet, powder, etc., and may be administered in various ways, including simple drinking, injection, spraying, squeezing, or the like.

MODE FOR INVENTION

The examples and experiments will now be described. The following examples and experiments are for illustrative purposes only and not intended to limit the scope of this disclosure.

Example 1

Preparation of *Astragalus membranaceus* Extract 8-year-old *Astragalus membranaceus* was harvested and crushed after washing and drying. *Astragalus membranaceus* was mixed with water and extracted at 80° C. for 6-8 hours in a vacuum high-pressure ceramic apparatus. The resulting extract was centrifuged and filtered to remove impurities. Then, 1,3-butylene glycol was added to prepare an *Astragalus membranaceus* extract.

Example 2

Preparation of *Saururus chinensis* Extract

The root of *Saururus chinensis* was washed, dried well, and then extracted for 7 days in 10 times the volume of ethanol at room temperature. The extract was filtered through a 250-mesh (3-μm) filter and then concentrated at 60° C. The concentrate was dissolved in water and ethyl acetate was added. After phase separation, the ethyl acetate layer was separated and concentrated again at 60° C. After adding methylene chloride to the concentrate, the resulting solution was precipitated twice in a mixture of ethyl acetate and hexane to remove impurities. After column fractionation, the resulting fraction was repeatedly concentrated at 60° C. and then at 30° C. under reduced pressure to completely remove the remaining solvent. Then, the resultant was dissolved in butylene glycol to a concentration of 2%. The resulting solution was further filtered and precipitated to prepare a *Saururus chinensis* extract.

Example 3

Preparation of *Glycyrrhizae radix* Extract

The root of *Glycyrrhizae radix* was washed well and extracted by immersing in ethanol. The extract was filtered and concentrated under reduced pressure.

The concentrated extract was re-extracted with ethyl acetate. The ethyl acetate fraction was separated using a resin column, filtered, concentrated and dried to prepare a *Glycyrrhizae radix* extract.

Example 4

Preparation of Rose Extract

The petal of rose was washed well, dried, and then extracted with hot water, propylene glycol or a mixture thereof. The resulting extract was repeatedly concentrated under reduced pressure and spray dried until the remaining solvent was completely removed and a rose extract was obtained as powder.

Example 5

Preparation of Rhubarb Extract

Rhubarb (1 kg) was added to purified water (20 kg) and extracted at 25° C. for 24 hours. After precipitating the extract at 0-4° C. for 24 hours, filtering through a 250-mesh filter and removing color and odor from the filtrate using activated carbon, the filtrate was further filtered repeatedly to prepare a rhubarb extract.

Example 6

Preparation of *Acanthopanax senticosus* Extract

*Acanthopanax senticosus* (1 kg) was added to purified water (20 kg) and extracted at 25° C. for 24 hours. After precipitating the extract at 0-4° C. for 24 hours, filtering through a 250-mesh filter and removing color and odor from the filtrate using activated carbon, the filtrate was further filtered repeatedly to prepare an *Acanthopanax senticosus* extract.

Example 7

Preparation of *Phellodendri* Cortex Extract

*Phellodendri* cortex (1 kg) was added to purified water (20 kg) and extracted at 25° C. for 24 hours. After precipitating the extract at 0-4° C. for 24 hours, filtering through a 250-mesh filter and removing color and odor from the filtrate using activated carbon, the filtrate was further filtered repeatedly to prepare a *Phellodendri* cortex extract.

Test Example 1

Cell Culturing

Sebocytes were acquired from the sebaceous gland of the ear of a 5-week-old male golden hamster according to Sato et al.'s method (*J Invest Dermatol* 2001, 117: 965-70). The sebocytes were cultured in a culture flask to $2.35 \times 10^4$ cells/cm$^2$.

The culture medium was prepared by adding 10% fetal bovine serum (JRH Bioscience, Tokyo, Japan) to DMEM/Ham's F12 medium (DMEM/F12) (1:1, Invitrogen, Carlsbad, Calif.) and then adding 0.68 mM L-glutamine (Invitrogen) and 10 nM recombinant human epidermal growth factor (rhEGF; Progen Biotechnik GmbH, Heidelberg, Germany).

100 mg/mL penicillin and 100 mg/mL streptomycin (both from Gibco, Milan, Italy) were used as antibiotics. It took 24 hours for the hamster sebocytes to completely adhere to the culture flask. Then, the cells were incubated at 37° C. and 5% $CO_2$.

Human keratinocyte cell line HaCaT was cultured under the condition of 37° C. and 5% $CO_2$ in DMEM medium (Invitrogen, Carlsbad, Calif.) wherein 10% fetal bovine serum (JRH Bioscience, Tokyo, Japan) and 100 mg/mL penicillin and 100 mg/mL streptomycin (both from Gibco, Milan, Italy) were added.

C57BL/6J mouse-derived melanocyte Melan-a cells were cultured under the condition of 37° C. and 10% $CO_2$ in RPMI-1640 medium (Invitrogen, Carlsbad, Calif.) wherein 10% fetal bovine serum (JRH Bioscience, Tokyo, Japan) and 200 nM tetradecanoylphorbol acetate (TPA), 100 mg/mL penicillin and streptomycin 100 mg/mL (all from Gibco, Milan, Italy) were added.

Test Example 2

Inhibition of Inflammatory Acne In Vitro

An in vitro inflammation model similar to the human acne environment was used with sebocytes and keratinocytes to effectively test the inflammatory acne inhibiting effect of the *Astragalus membranaceus, Saururus chinensis, Glycyrrhizae radix*, rose, rhubarb, *Acanthopanax senticosus* and *Phellodendri* cortex extracts. HaCaT keratinocytes and golden hamster sebocytes were seeded on a 24-well culture plate, with $3.75 \times 10^4$ cells and $6.0 \times 10^4$ cells, respectively. The cells were allowed to adhere to the bottom of the culture plate for one day. The culture medium was prepared by adding 10% fetal bovine serum (JRH Bioscience, Tokyo, Japan) to DMEM/Ham's F12 medium (1:1, Invitrogen, Carlsbad, Calif.) and then adding 100 mg/mL penicillin and 100 mg/mL streptomycin (both from Gibco, Milan, Italy).

After one day, the cells were treated with 50 μM linoleic acid, 50 μM arachidonic acid, 10 nM dihydrotestosterone, and 0.5% *Propionibacterium acnes* (*P. acnes*) as stimulants to induce inflammatory acne. At the same time, the cells were treated with *Astragalus membranaceus, Saururus chinensis, Glycyrrhizae radix*, rose, rhubarb, *Acanthopanax senticosus* or *Phellodendri* cortex extract, and their inflammatory acne inhibiting effect was investigated. DMSO was used as negative control, and 100 nM isotretinoin, which is a prescription drug used to treat acne, was used as positive control. One day after the treatment with the stimulants and the extracts, the concentration of the inflammatory cytokines (granulocyte macrophage colony-stimulating factor (GM-CSF)), interleukin-1 alpha (IL-1α), interleukin-8 (IL-8) and tumor necrosis factor-alpha (TNF-α) released from the culture medium was measured by multiplex bead-based cytokine assay in a 50 μl medium.

Specifically, the procedure was as follows. After wetting a 96-well filter plate with a washing buffer, the solution was completely removed using a vacuum pump. Then, the cell culture medium was reacted for 30 minutes with antibody-conjugated beads. After the reaction was completed, detection antibody was added and reaction was performed for another 30 minutes. Then, streptavidin-phycoerythrin (PE) was added to each well. After waiting for 30 minutes, the streptavidin-PE remaining unattached was removed using a washing buffer and the quantity of the cytokines attached to the beads was measuring using Bio-Plex 200.

Figure 2:
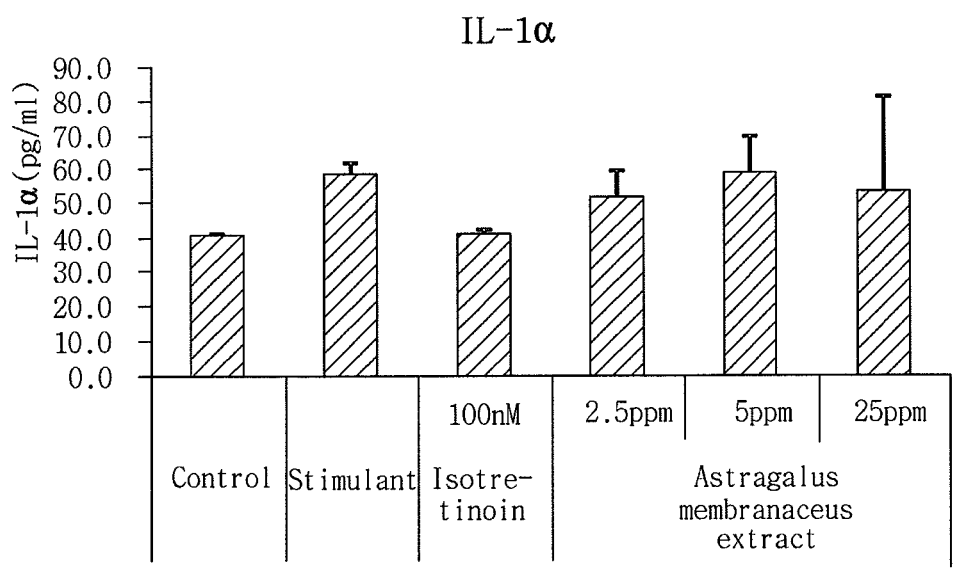
Figure 3:
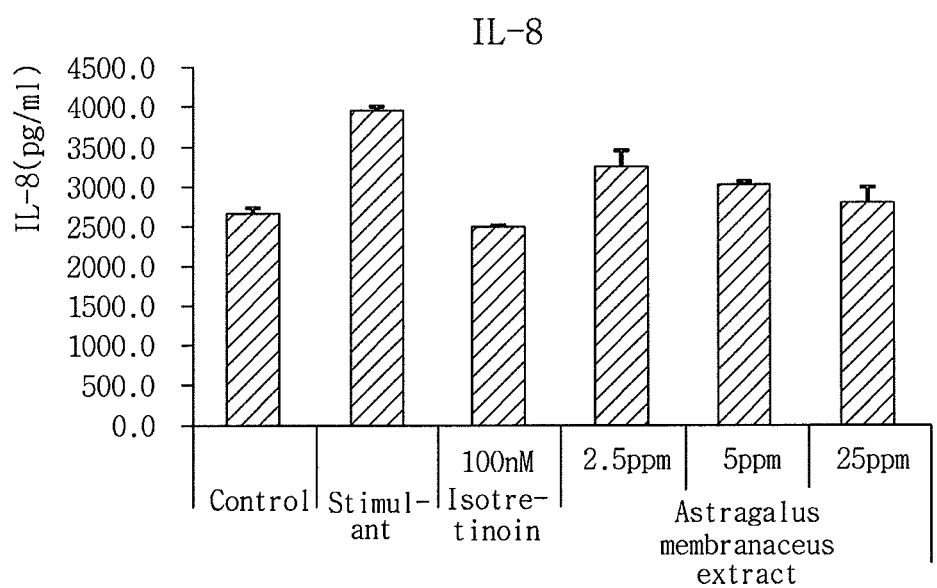
Figure 4:
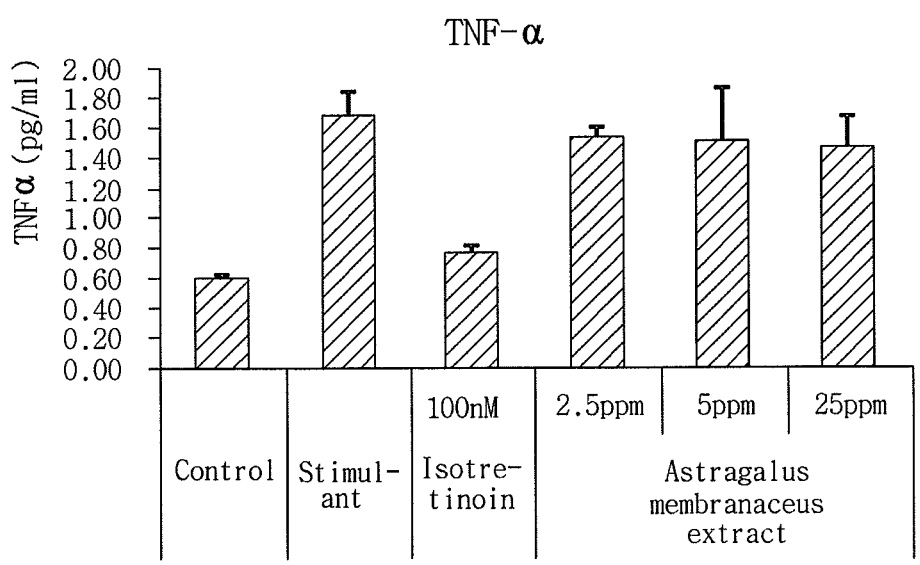

The result for the *Astragalus membranaceus* extract is shown in FIG. 1 (GM-CSF), FIG. 2 (IL-1α), FIG. 3 (IL-8) and FIG. 4 (TNF-α). Referring to FIGS. 1-4, the *Astragalus membranaceus* extract inhibits the inflammatory cytokines in a concentration-dependent manner. Especially, as seen from FIG. 1, the *Astragalus membranaceus* extract inhibits GM-SCF comparably to the prescription drug isotretinoin.

Figure 5:
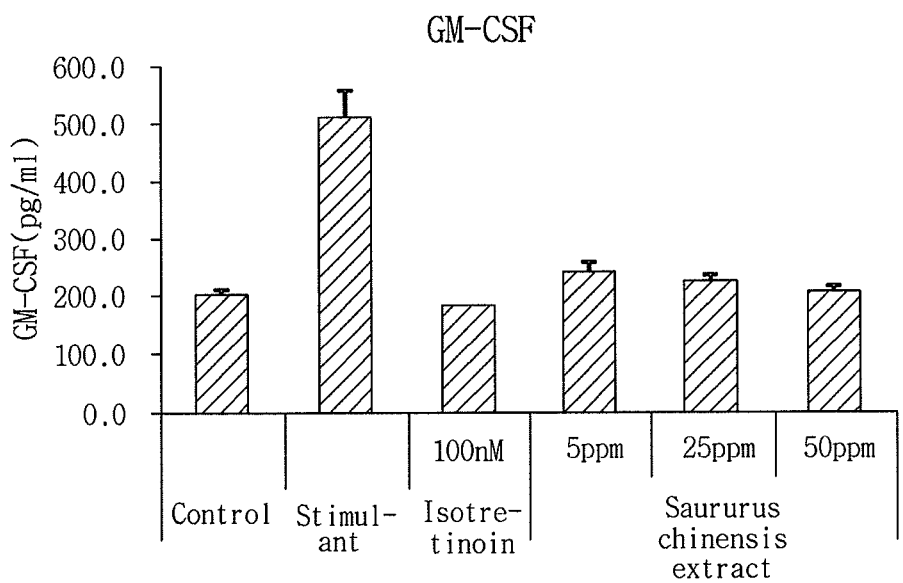
FIGS. 5-8 show inflammatory cytokine inhibiting effect of a *Saururus chinensis* extract for GM-CSF (FIG. 5), IL-1α (FIG. 6), IL-8 (FIG. 7) and TNF-α (FIG. 8)
Figure 6:
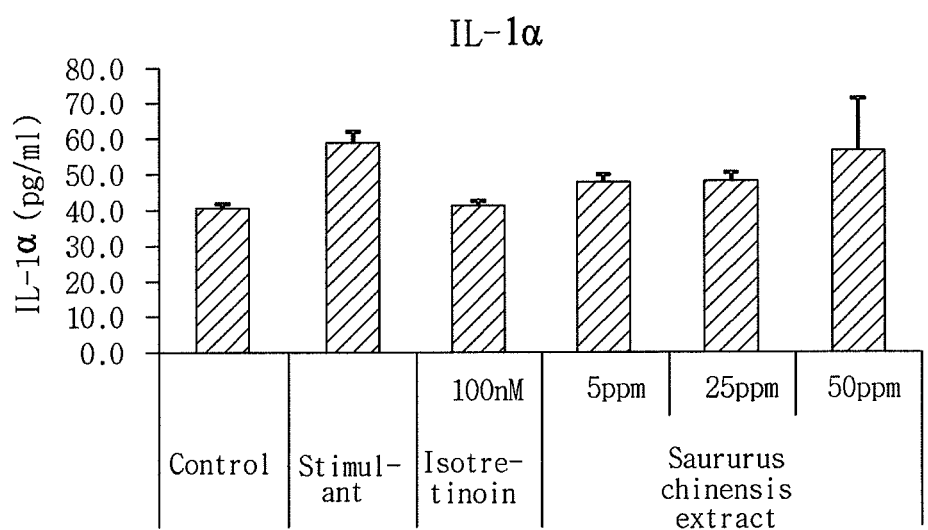
Figure 7:
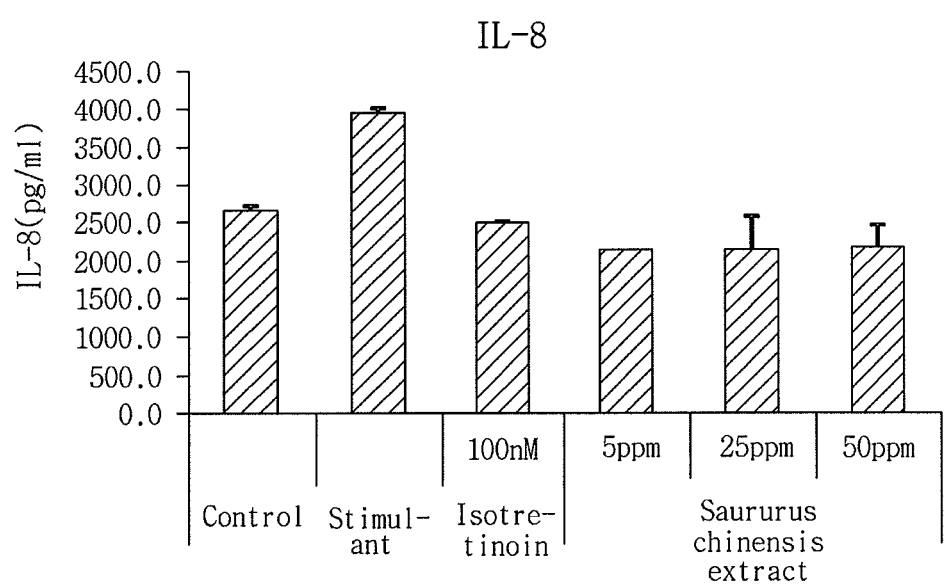
Figure 8:
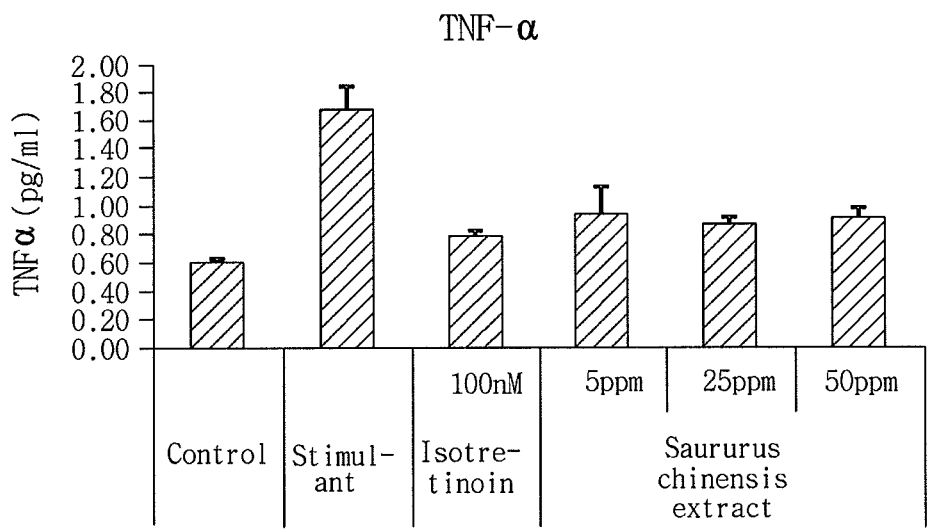

The result for the *Saururus chinensis* extract is shown in FIG. 5 (GM-CSF), FIG. 6 (IL-1α), FIG. 7 (IL-8) and FIG. 8 (TNF-α). Referring to FIGS. 5-8, the *Saururus chinensis* extract inhibits the inflammatory cytokines in a concentration-dependent manner. As seen from FIG. 6, the effect for IL-1α was superior only below 50 ppm.

Figure 9:
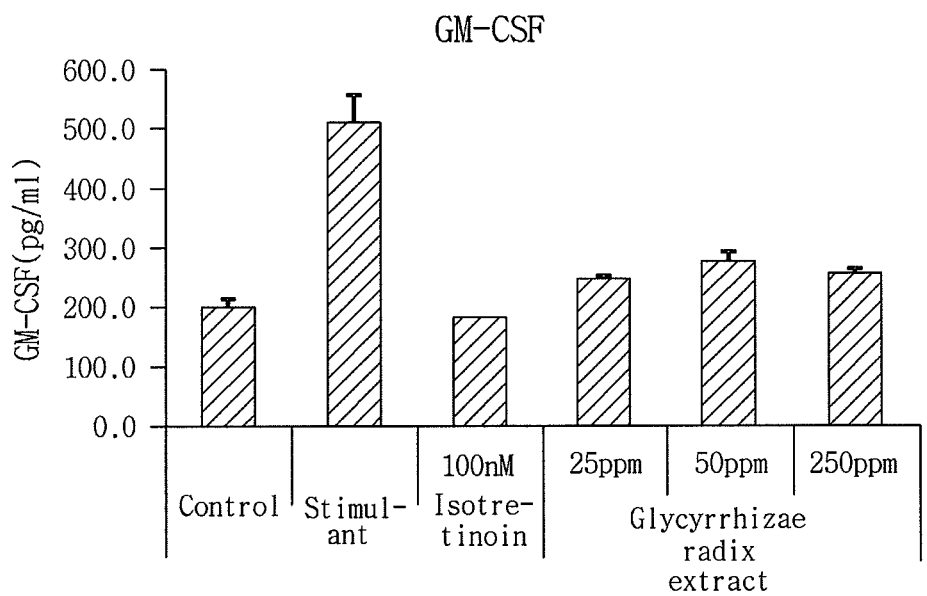
FIGS. 9-12 show inflammatory cytokine inhibiting effect of a *Glycyrrhizae radix* extract for GM-CSF (FIG. 9), IL-1α (FIG. 10), IL-8 (FIG. 11) and TNF-α (FIG. 12)
Figure 10:
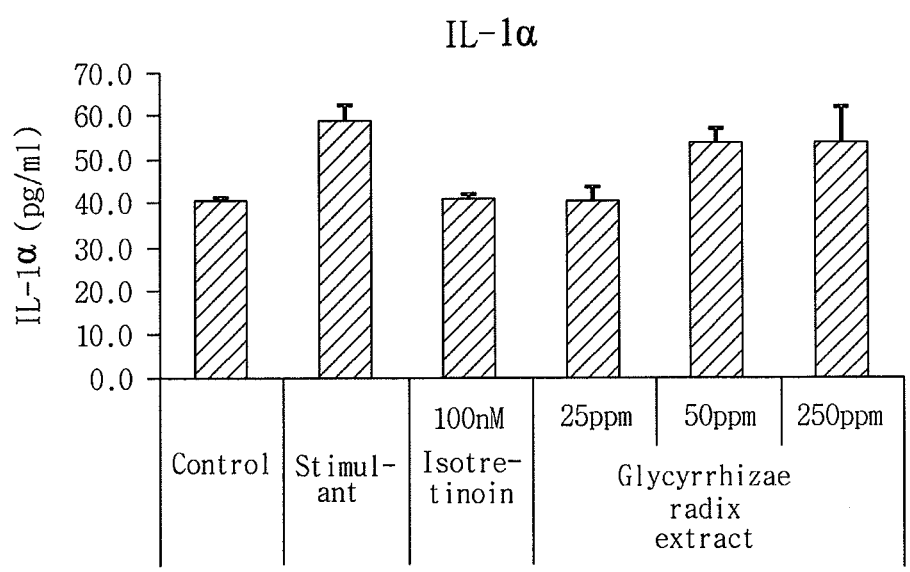
Figure 11:
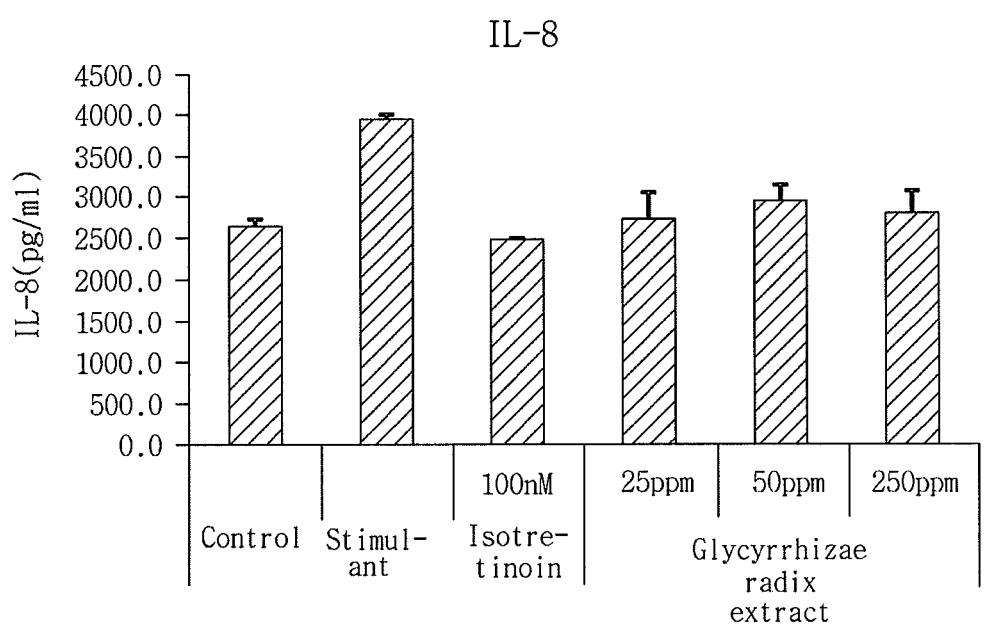
Figure 12:
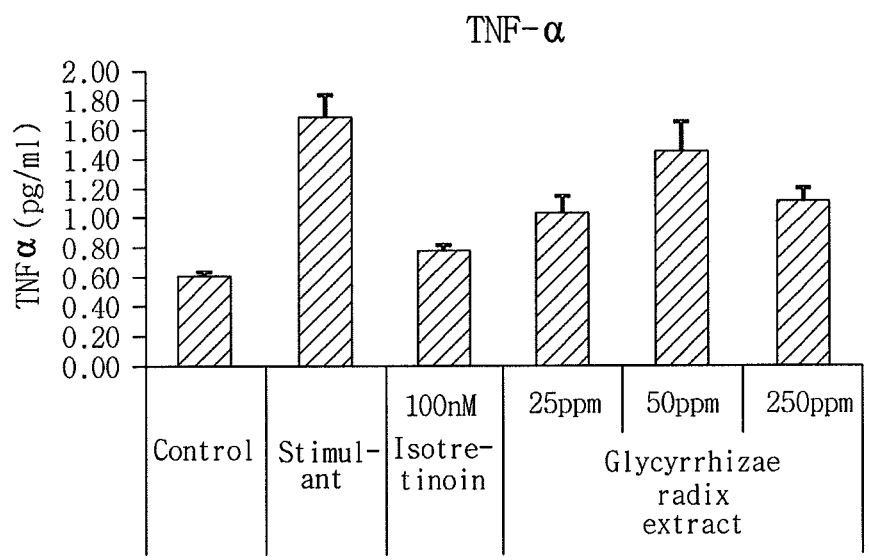

The result for the *Glycyrrhizae radix* extract is shown in FIG. 9 (GM-CSF), FIG. 10 (IL-1α), FIG. 11 (IL-8) and FIG. 12 (TNF-α). Referring to FIGS. 9-12, the *Glycyrrhizae radix* extract shows the best inflammatory cytokine inhibiting effect at 25 ppm. Accordingly, it can be seen that the *Glycyrrhizae radix* extract effectively inhibits the inflammatory cytokines even at relatively low concentrations.

Figure 13:
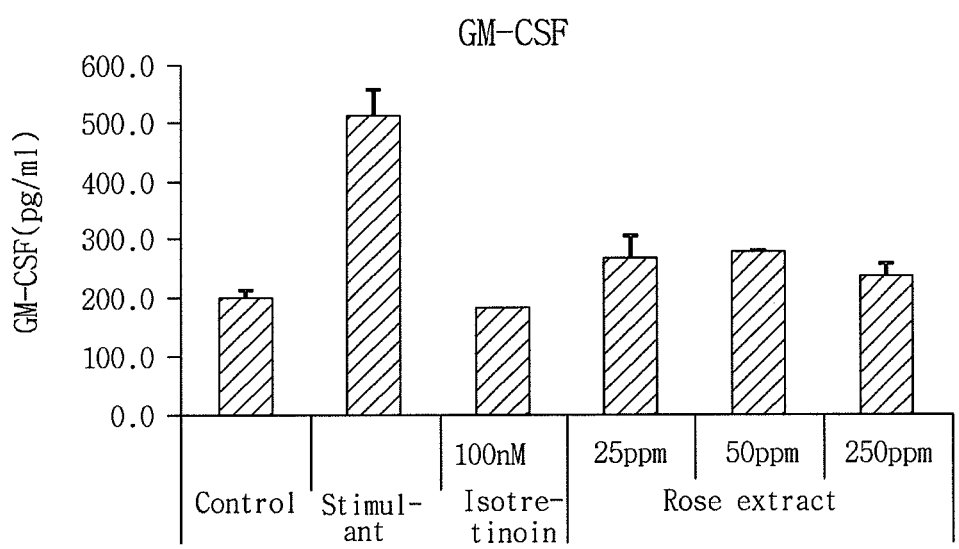
FIGS. 13-16 show inflammatory cytokine inhibiting effect of a rose extract for GM-CSF (FIG. 13), IL-1α (FIG. 14), IL-8 (FIG. 15) and TNF-α (FIG. 16)
Figure 14:
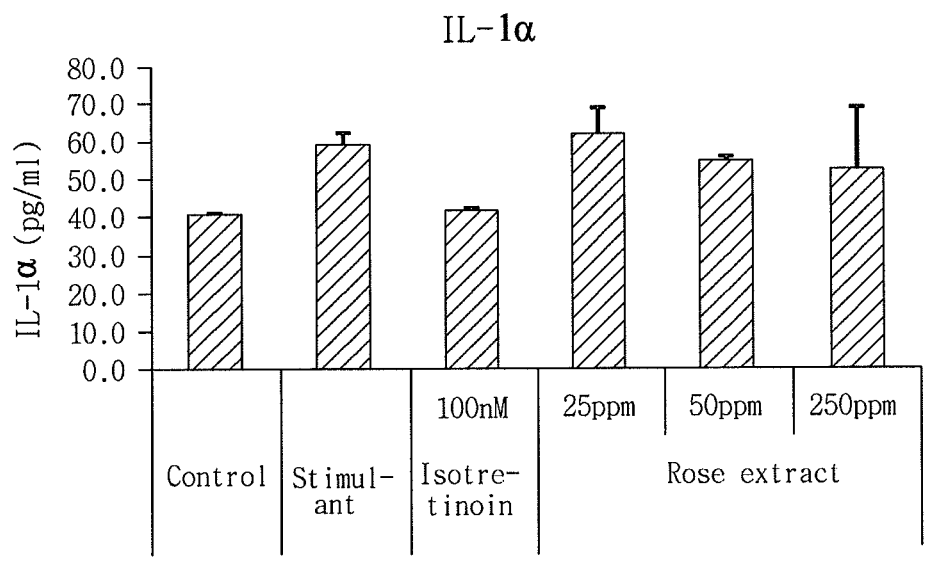
Figure 15:
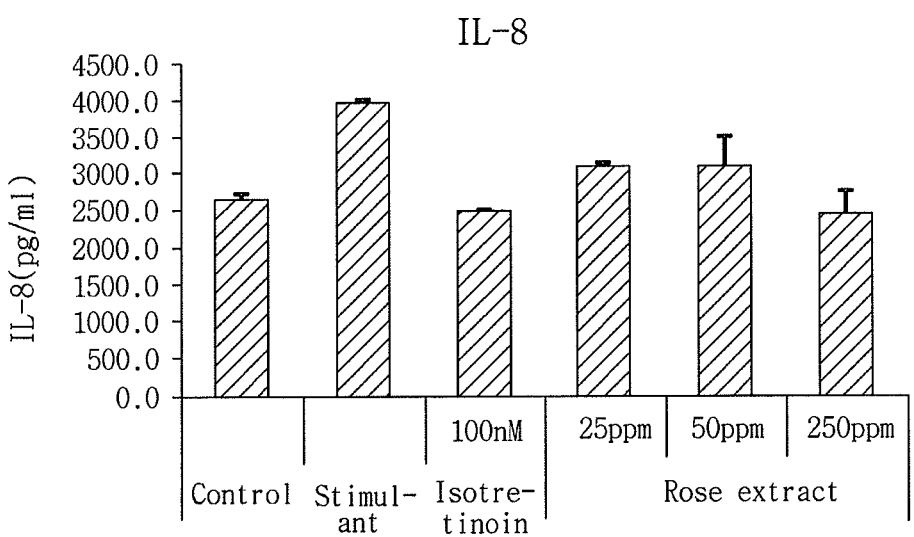
Figure 16:
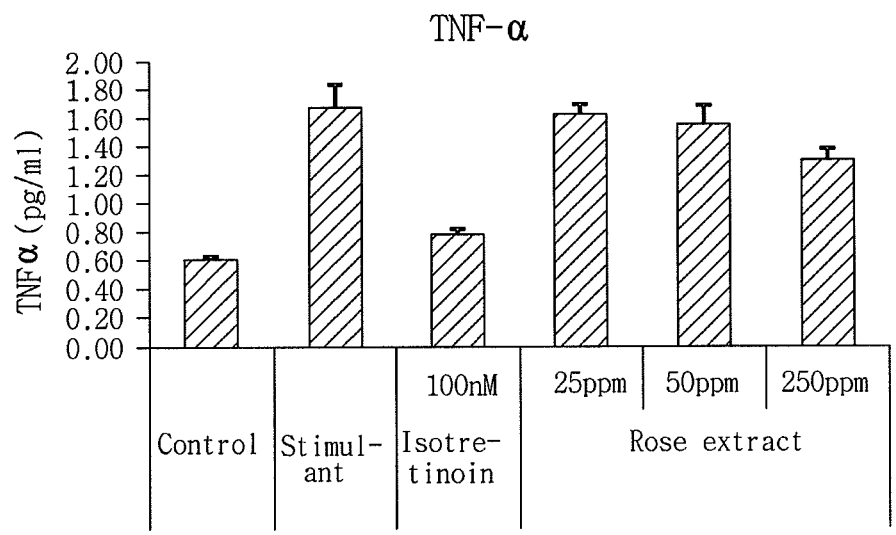

The result for the rose extract is shown in FIG. 13 (GM-CSF), FIG. 14 (IL-1α), FIG. 15 (IL-8) and FIG. 16 (TNF-α). Referring to FIGS. 13-16, the rose extract inhibits the inflammatory cytokines in a concentration-dependent manner.

Figure 17:
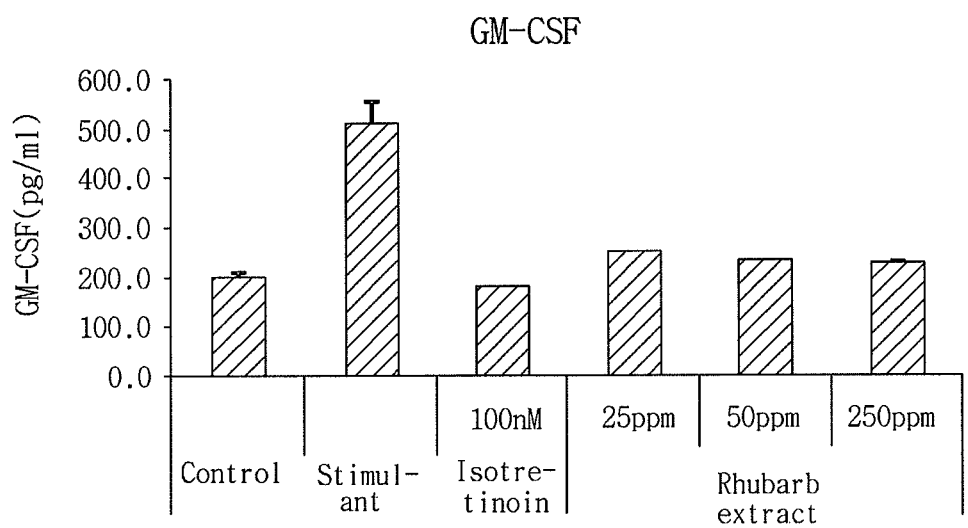
FIGS. 17-20 show inflammatory cytokine inhibiting effect of a rhubarb extract for GM-CSF (FIG. 17), IL-1α (FIG. 18), IL-8 (FIG. 19) and TNF-α (FIG. 20)
Figure 18:
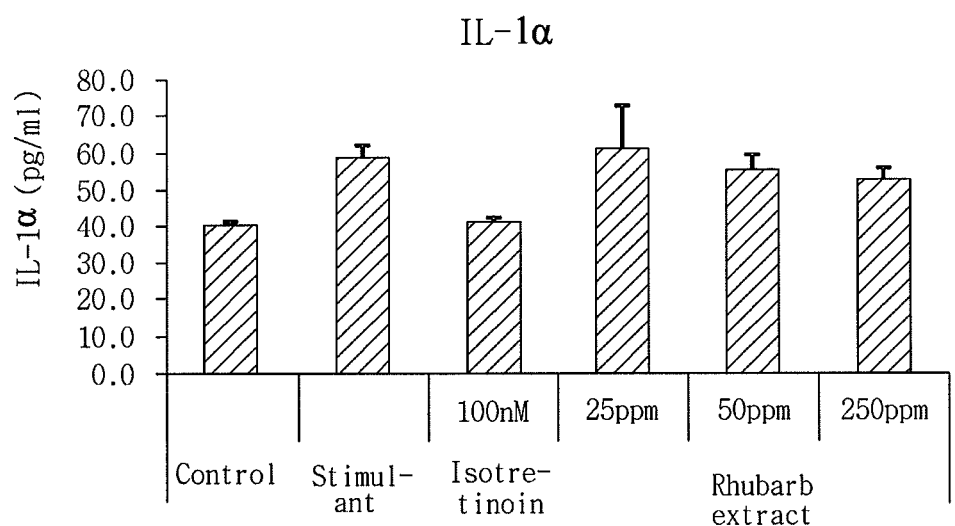
Figure 19:
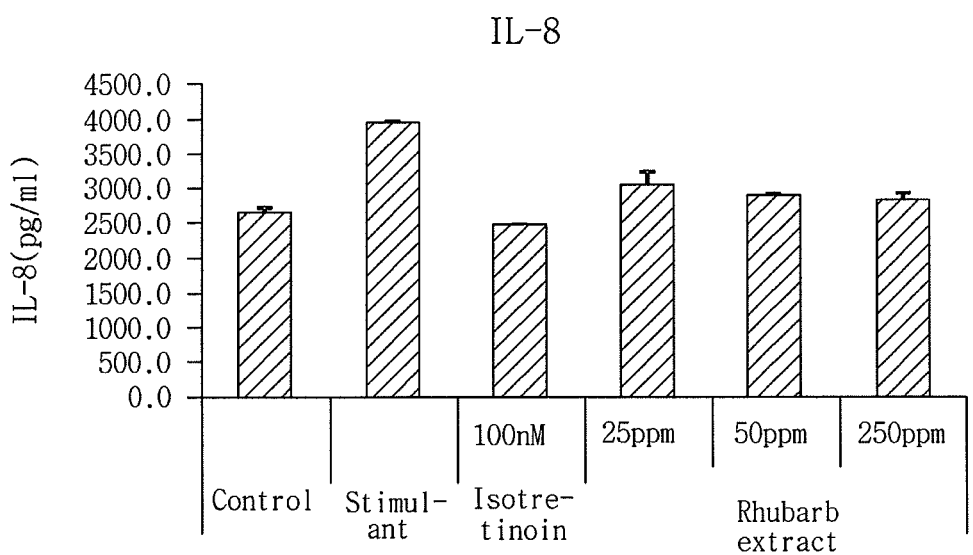
Figure 20:
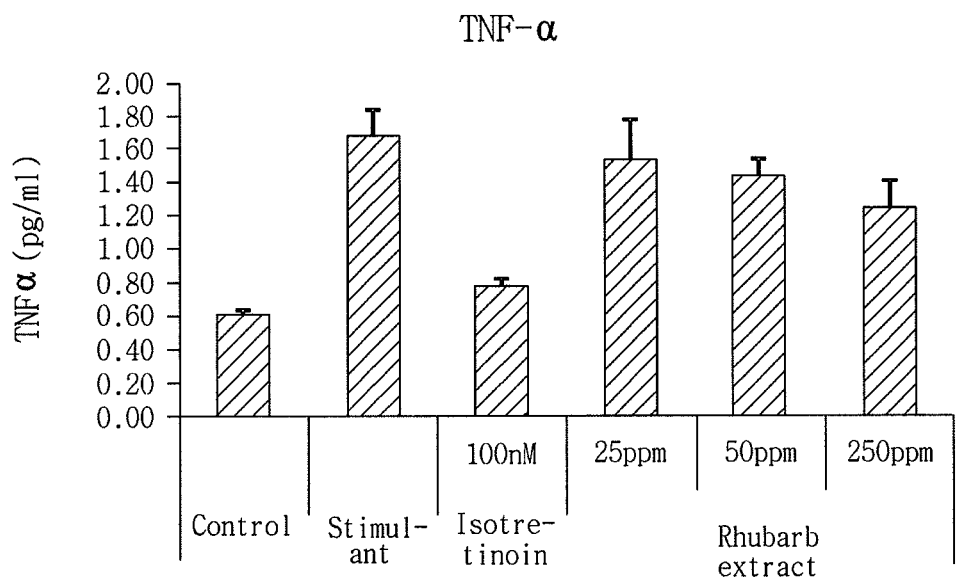

The result for the rhubarb extract is shown in FIG. 17 (GM-CSF), FIG. 18 (IL-1α), FIG. 19 (IL-8) and FIG. 20 (TNF-α). Referring to FIGS. 17-20, the rhubarb extract inhibits the inflammatory cytokines in a concentration-dependent manner.

Figure 21:
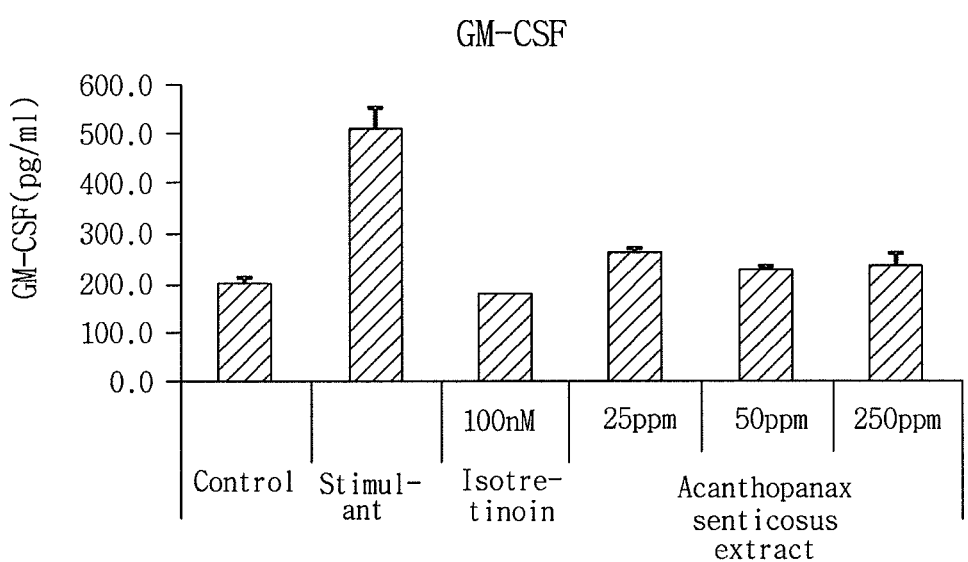
FIGS. 21-24 show inflammatory cytokine inhibiting effect of an *Acanthopanax senticosus* extract for GM-CSF (FIG. 21), IL-1α (FIG. 22), IL-8 (FIG. 23) and TNF-α (FIG. 24)
Figure 22:
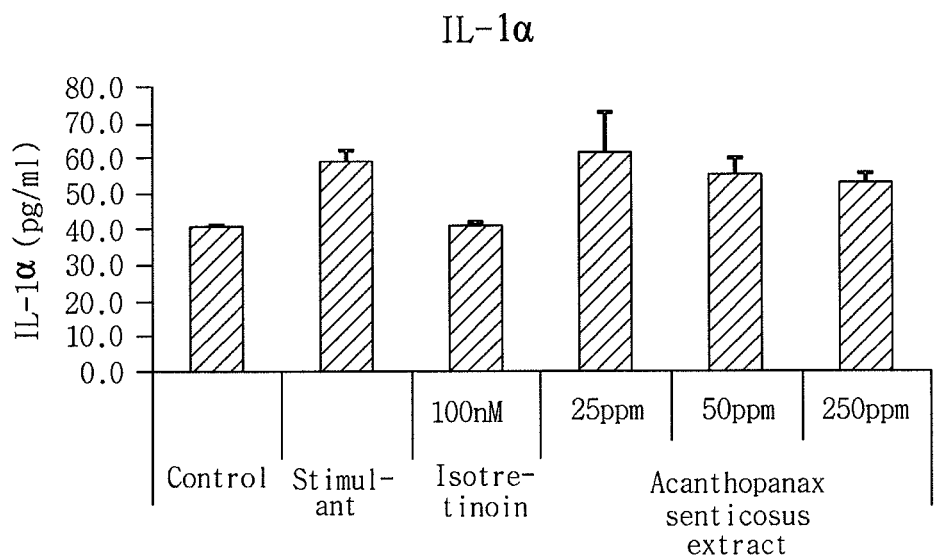
Figure 23:
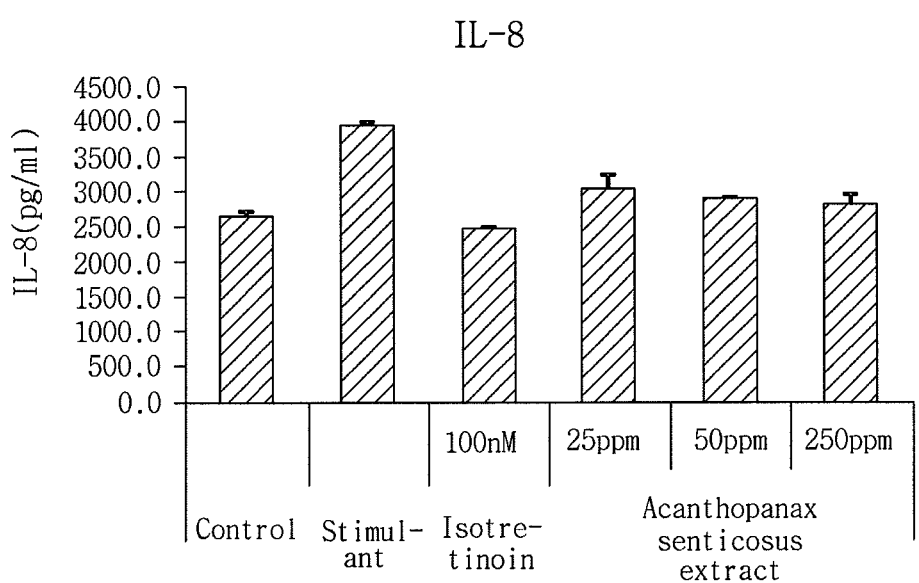
Figure 24:
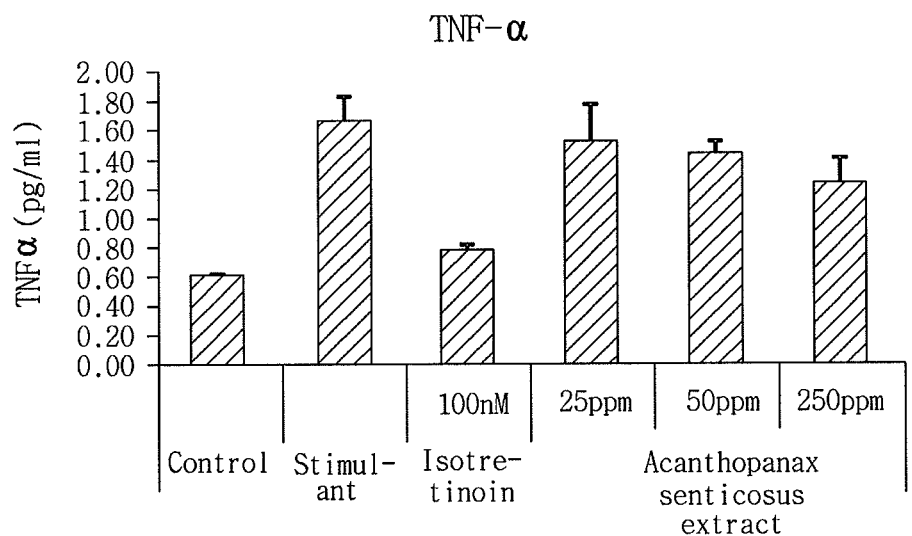

The result for the *Acanthopanax senticosus* extract is shown in FIG. 21 (GM-CSF), FIG. 22 (IL-1α), FIG. 23 (IL-8) and FIG. 24 (TNF-α). Referring to FIGS. 21-24, the *Acanthopanax senticosus* extract inhibits the inflammatory cytokines in a concentration-dependent manner.

Figure 25:
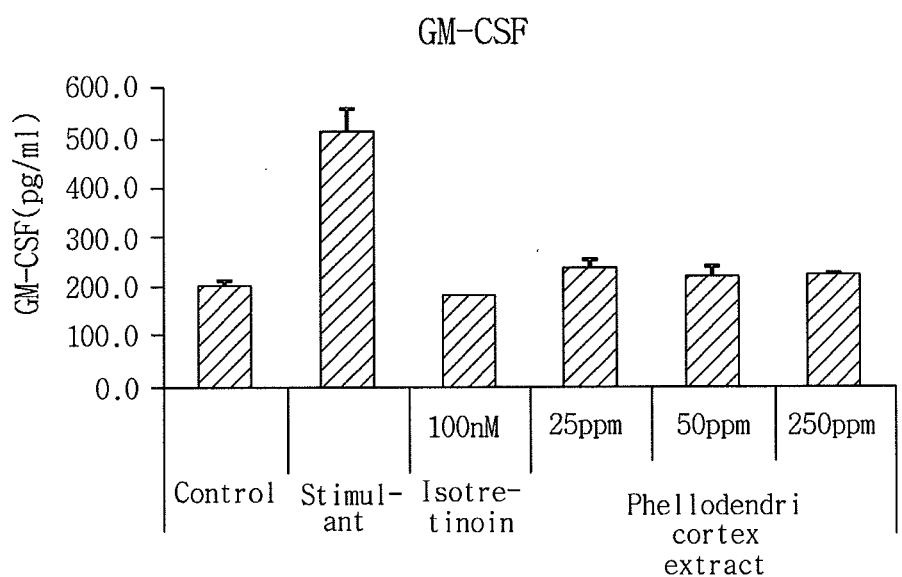
FIGS. 25-28 show inflammatory cytokine inhibiting effect of an *Phellodendri* cortex extract for GM-CSF (FIG. 25), IL-1α (FIG. 26), IL-8 (FIG. 27) and TNF-α (FIG. 28)
Figure 26:
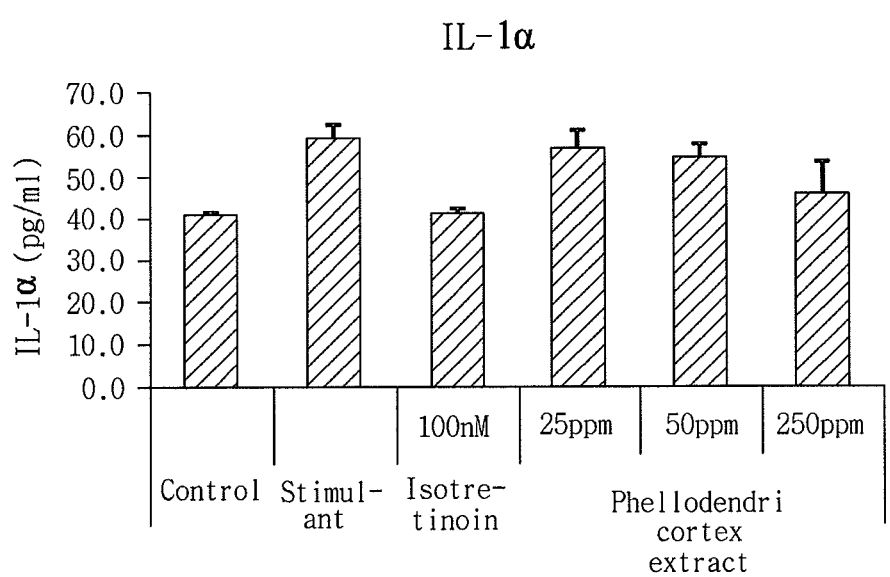
Figure 27:
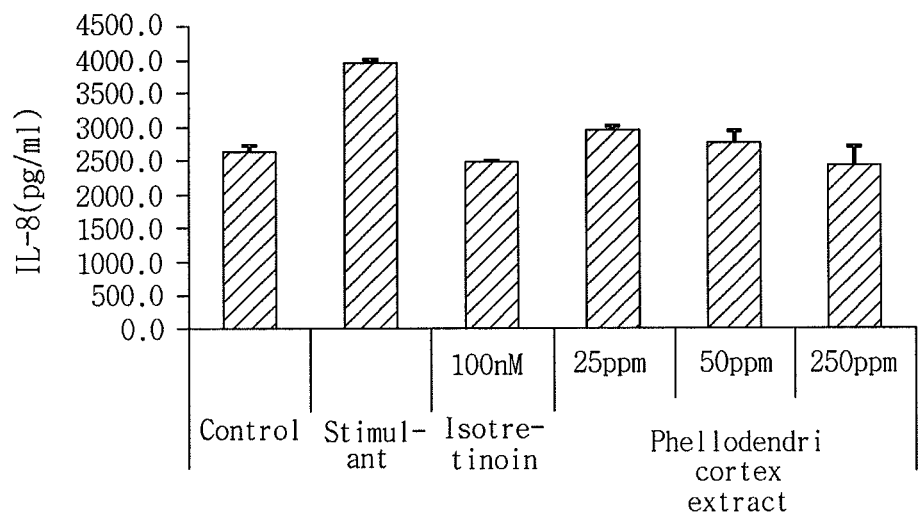
Figure 28:
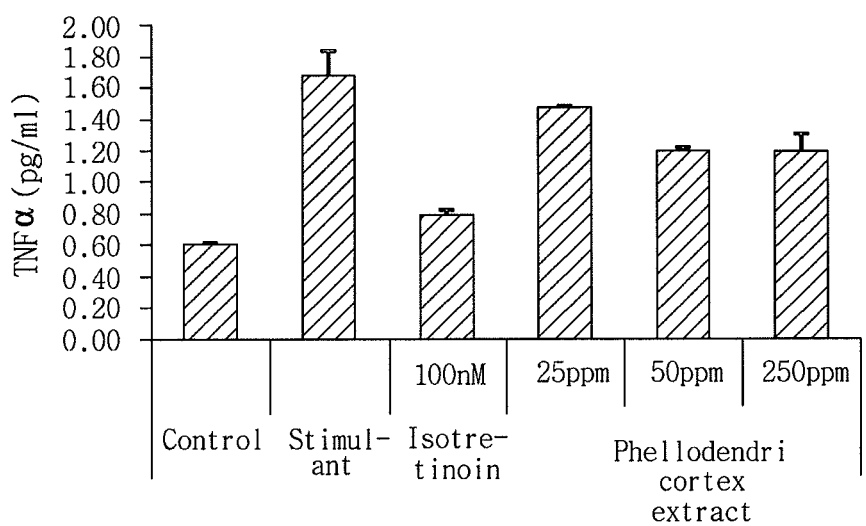

And, the result for the *Phellodendri* cortex extract is shown in FIG. 25 (GM-CSF), FIG. 26 (IL-1α), FIG. 27 (IL-8) and FIG. 28 (TNF-α). Referring to FIGS. 25-28, the *Phellodendri* cortex extract inhibits the inflammatory cytokines in a concentration-dependent manner.

Test Example 3

Inhibition of Sebum Production In Vitro

An in vitro inflammation model similar to the human acne environment was used with sebocytes and keratinocytes to effectively test the sebum production inhibiting effect of the *Astragalus membranaceus, Saururus chinensis, Glycyrrhizae radix*, rose, rhubarb, *Acanthopanax senticosus* and *Phellodendri* cortex extracts. HaCaT keratinocytes and golden hamster sebocytes were seeded on a 24-well culture plate, with $3.75 \times 10^4$ cells and $6.0 \times 10^4$ cells, respectively. The cells were allowed to adhere to the bottom of the culture plate for one day. The culture medium was prepared by adding 10% fetal bovine serum (JRH Bioscience, Tokyo, Japan) to DMEM/Ham's F12 medium (1:1, Invitrogen, Carlsbad, Calif.) and then adding 100 mg/mL penicillin and 100 mg/mL streptomycin (both from Gibco, Milan, Italy).

After one day, the cells were treated with 50 μM linoleic acid, 50 μM arachidonic acid, 10 nM dihydrotestosterone, and 0.5% *Propionibacterium acnes* (*P. acnes*) as stimulants to induce inflammatory acne. At the same time, the cells were treated with *Astragalus membranaceus, Saururus chinensis, Glycyrrhizae radix*, rose, rhubarb, *Acanthopanax senticosus* or *Phellodendri* cortex extract respectively, and their sebum production inhibiting effect was investigated. DMSO was used as negative control, and 100 nM isotretinoin, which is a prescription drug used to treat acne, was used as positive control. One day after the treatment with the stimulants and the extracts, the quantity of neutral lipids produced in the cells was measured by Oil Red O staining.

Specifically, the procedure was as follows. The cells were washed with PBS and fixed in a 3.7% formaldehyde solution for 30 minutes. The fixed cells were washed 3 times with PBS and once with 70% ethanol and then stained with 0.4% Oil Red 0 solution for 30 minutes. The stained cells were washed once with 70% ethanol and then 3 times with PBS. Then, after dissolving the Oil Red O solution with isopropanol, absorbance was measured at 520 nm using a spectrophotometer.

Figure 29:
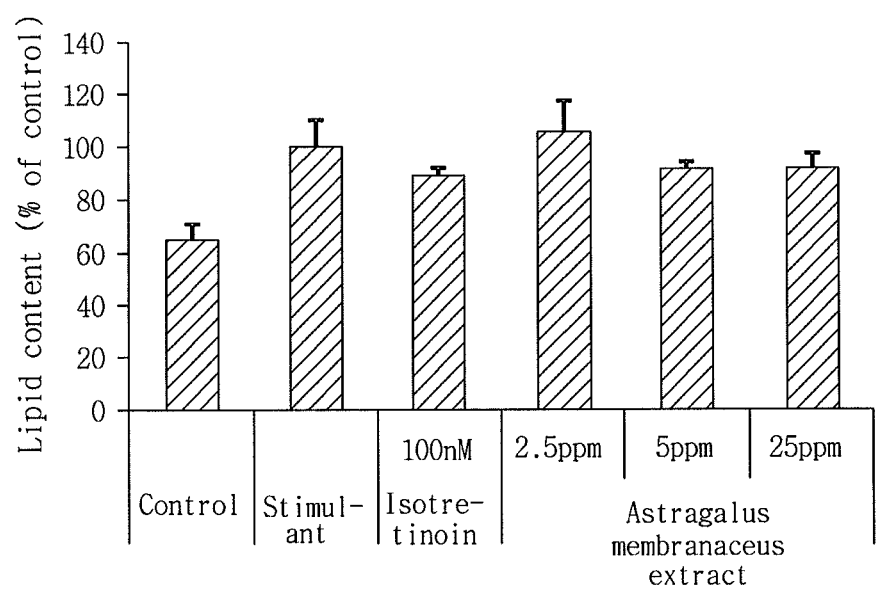
FIG. 29 shows sebum production inhibiting effect of an *Astragalus membranaceus* extract.

The result for the *Astragalus membranaceus* extract is shown in FIG. 29. Referring to FIG. 29, the *Astragalus membranaceus* extract is effective in inhibiting sebum production. Especially, it exhibits superior sebum production inhibiting effect at 5 ppm or above.

Figure 30:
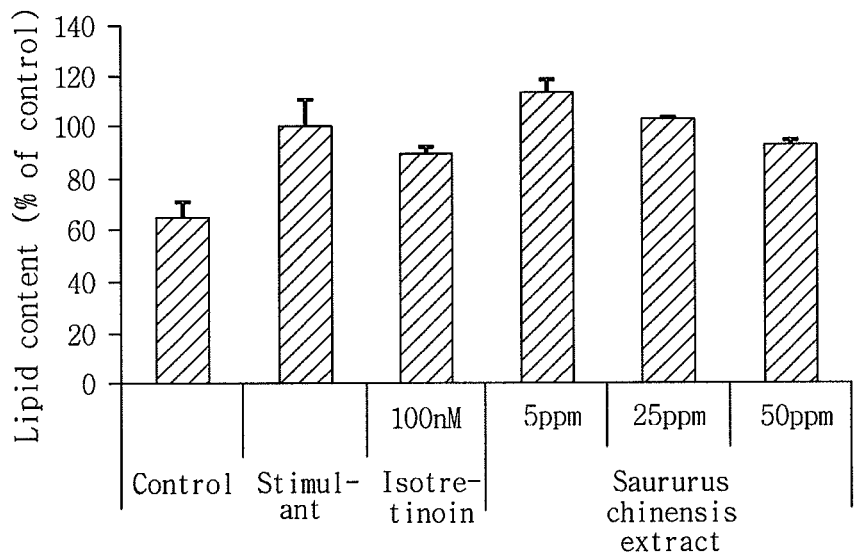
FIG. 30 shows sebum production inhibiting effect of a *Saururus chinensis* extract.

The result for the *Saururus chinensis* extract is shown in FIG. 30. Referring to FIG. 30, the *Saururus chinensis* extract inhibits sebum production in a concentration-dependent manner. It exhibits significant sebum production inhibiting effect at 50 ppm or above.

Figure 31:
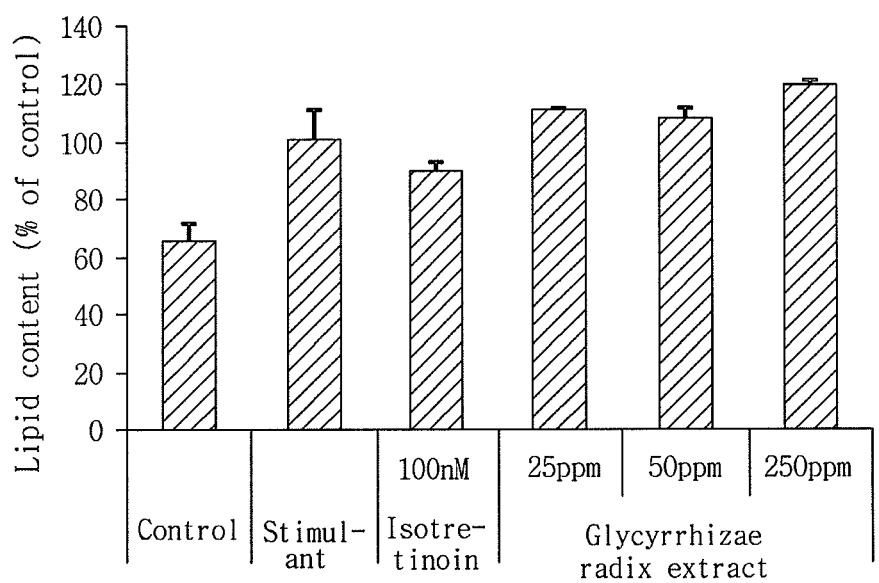
FIG. 31 shows sebum production inhibiting effect of a *Glycyrrhizae radix* extract.

The result for the *Glycyrrhizae radix* extract is shown in FIG. 31. Referring to FIG. 31, the *Glycyrrhizae radix* extract exhibits sebum inhibiting effect even at relatively low concentrations.

Figure 32:
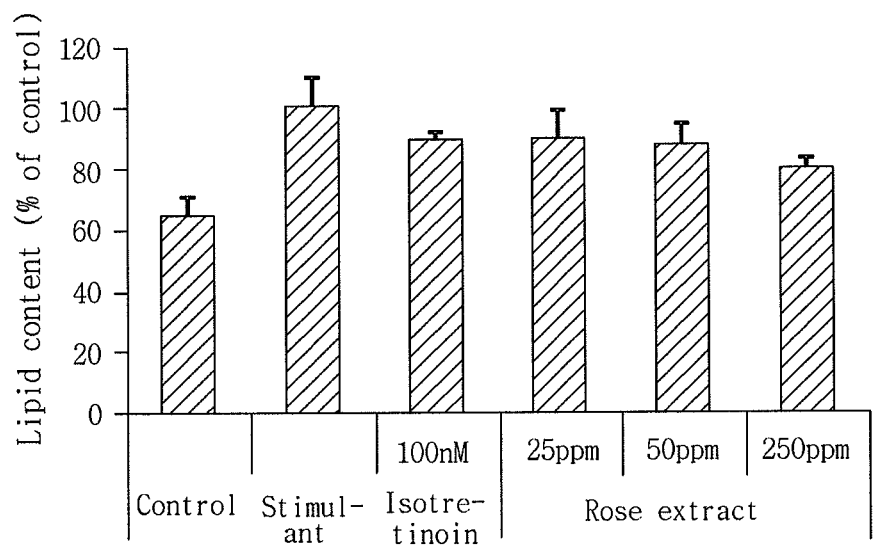
FIG. 32 shows sebum production inhibiting effect of a rose extract.

The result for the rose extract is shown in FIG. 32. Referring to FIG. 32, the rose extract inhibits sebum production in a concentration-dependent manner.

Figure 33:
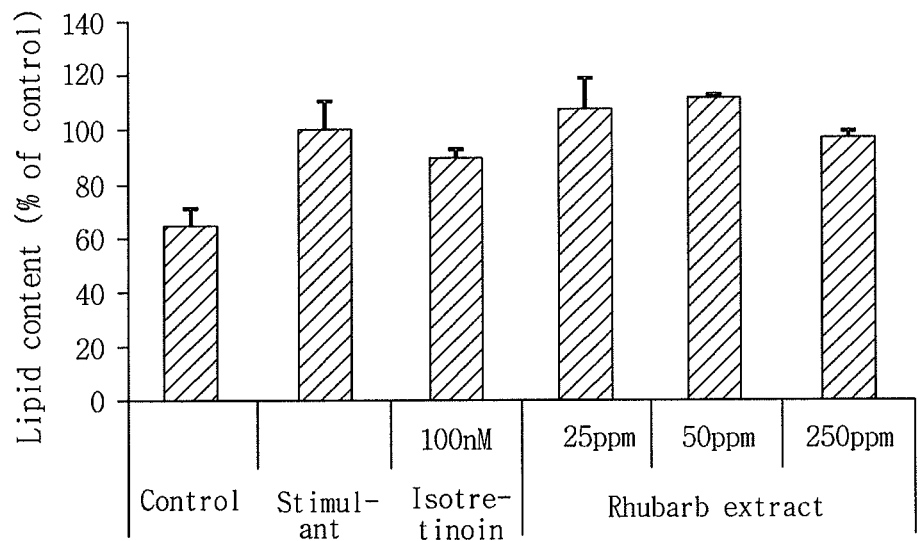
FIG. 33 shows sebum production inhibiting effect of a rhubarb extract.

The result for the rhubarb extract is shown in FIG. 33. Referring to FIG. 33, the rhubarb extract inhibits sebum production in a concentration-dependent manner.

Figure 34:
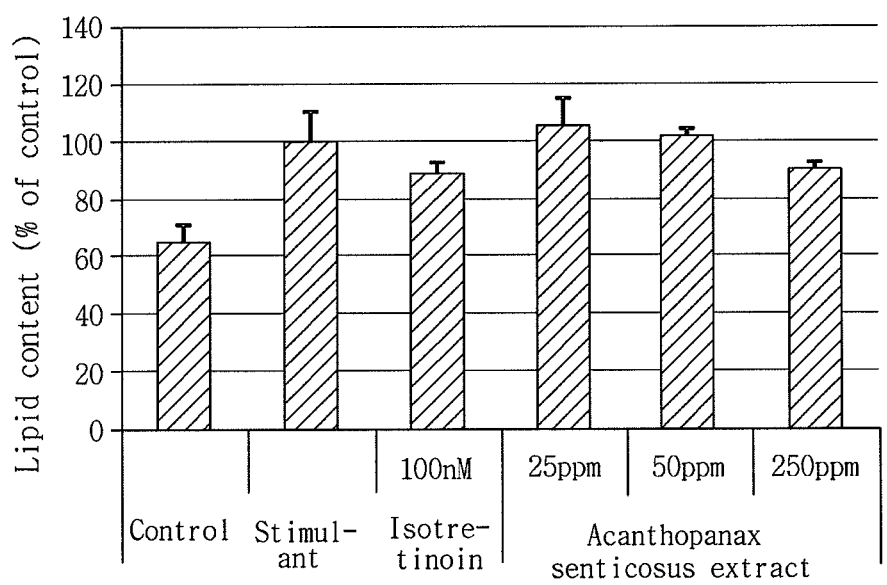
FIG. 34 shows sebum production inhibiting effect of an *Acanthopanax senticosus* extract.

The result for the *Acanthopanax senticosus* extract is shown in FIG. 34. Referring to FIG. 34, the *Acanthopanax senticosus* extract inhibits sebum production in a concentration-dependent manner.

Figure 35:
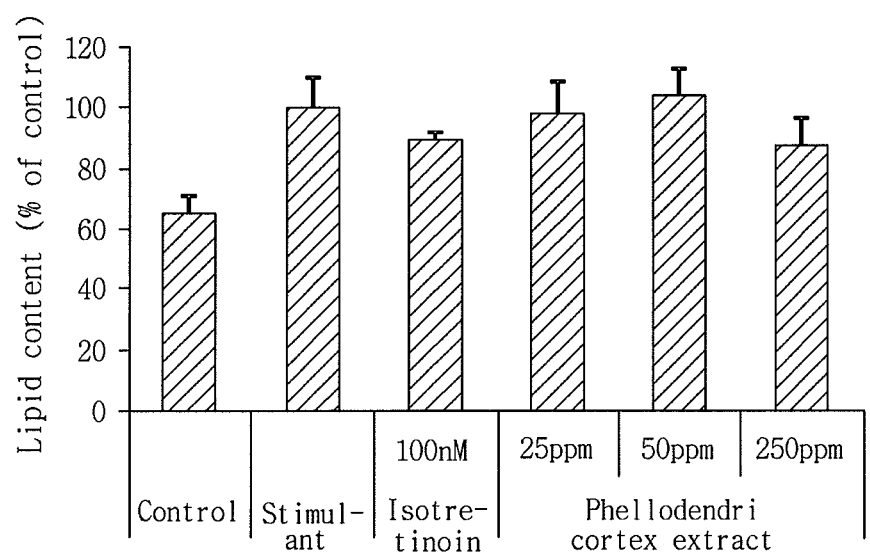
FIG. 35 shows sebum production inhibiting effect of a *Phellodendri* cortex extract.

And, the result for the *Phellodendri* cortex extract is shown in FIG. 35. Referring to FIG. 35, the *Phellodendri* cortex extract inhibits sebum production in a concentration-dependent manner. Especially, it exhibits significant sebum production inhibiting effect at 250 ppm.

Test Example 4

Inhibition of Acnegenic Pigmentation In Vitro

An in vitro model similar to the environment of pigmentation induced from inflammatory acne of human was used with melanocytes to effectively test the acnegenic pigmentation inhibiting effect of the *Astragalus membranaceus, Saururus chinensis, Glycyrrhizae radix*, rose, rhubarb, *Acanthopanax senticosus* and *Phellodendri* cortex extracts. $5.0 \times 10^4$ Melan-a melanocytes were seeded on a 24-well culture plate. The cells were allowed to adhere to the bottom of the culture plate for one day. The culture medium was prepared by adding 10% fetal bovine serum (JRH Bioscience, Tokyo, Japan) to RPM I-1640 (Invitrogen, Carlsbad, Calif.) and then adding 200 nM tetradecanoyl phorbol acetate (TPA), 100 mg/mL penicillin and 100 mg/mL streptomycin (all from Gibco, Milan, Italy).

After one day, the cells were treated with 50 µM linoleic acid, 50 µM arachidonic acid, 10 nM dihydrotestosterone, and 0.5% *Propionibacterium acnes* (*P. acnes*) as stimulants to induce acnegenic pigmentation and cultured for 5 days. Then, the cells were treated with *Astragalus membranaceus, Saururus chinensis, Glycyrrhizae radix*, rose, rhubarb, *Acanthopanax senticosus* or *Phellodendri* cortex extract respectively, and their acnegenic pigmentation inhibiting effect was investigated. DMSO was used as negative control, and 1 µM hydroquinone and 200 ppm kojic acid were used as positive control. Hydroquinone is a prescription drug used as a melanin inhibitor. And, kojic acid has whitening effect and is often used in cosmetic compositions. However, kojic acid may cause strong stimulation to the skin and is recently reported to have the possibility of causing various cancers. 5 days after the treatment with the extracts, melanin was dissolved by treating with 1 N NaOH and absorbance was measured at 405 nm using a spectrophotometer.

Figure 36:
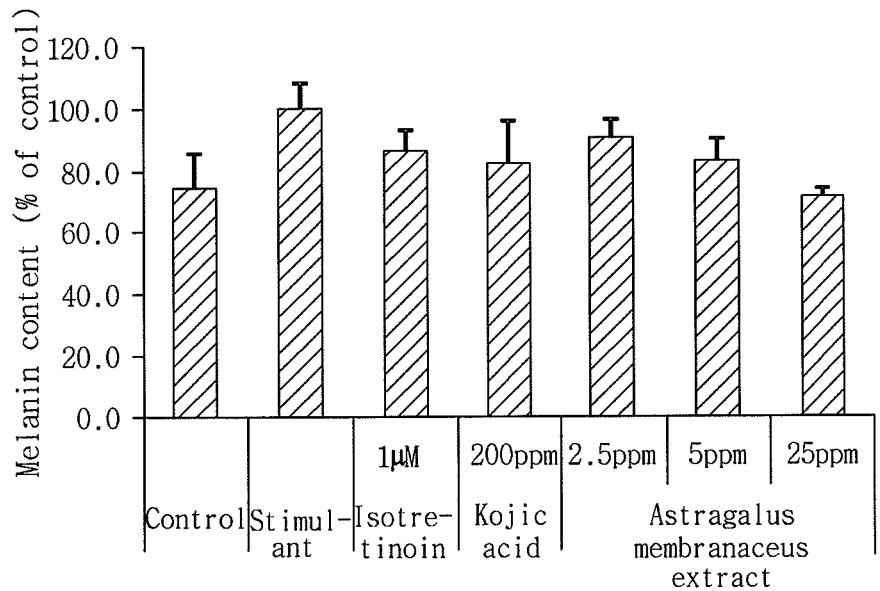
FIG. 36 shows acnegenic pigmentation inhibiting effect of an *Astragalus membranaceus* extract.

The result for the *Astragalus membranaceus* extract is shown in FIG. 36. Referring to FIG. 36, the *Astragalus membranaceus* extract inhibits pigmentation in a concentration-dependent manner. At 5 ppm, the degree of pigmentation was even lower than hydroquinone which is used as a prescription drug. Especially, at 25 ppm, the degree of pigmentation was even lower than the control group not treated with any stimulant. Accordingly, it can be seen that the *Astragalus membranaceus* extract has superior pigmentation inhibiting effect and skin whitening effect.

Figure 37:
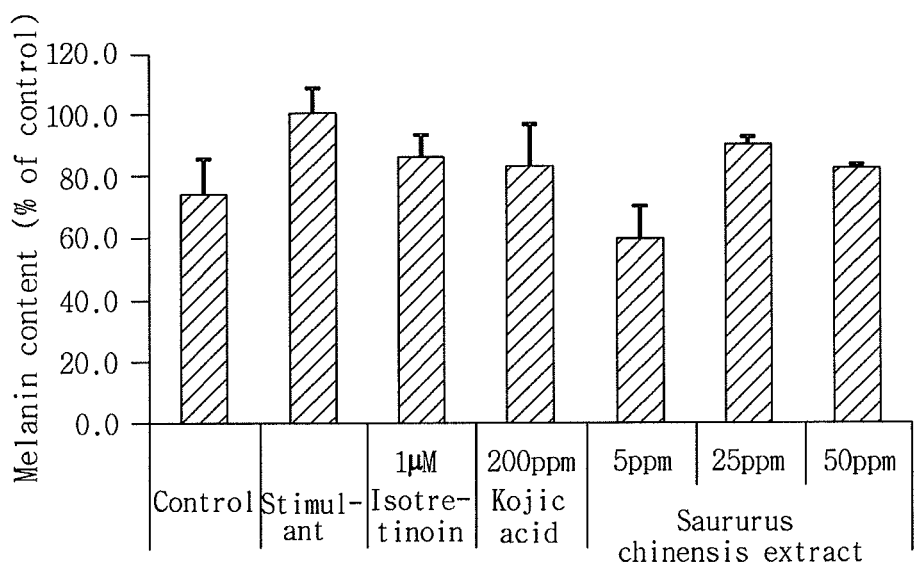
FIG. 37 shows acnegenic pigmentation inhibiting effect of a *Saururus chinensis* extract.

The result for the *Saururus chinensis* extract is shown in FIG. 37. Referring to FIG. 37, the *Saururus chinensis* extract inhibits pigmentation in a concentration-dependent manner. Especially, at 5 ppm, the pigmentation inhibiting effect was very superior, with the degree of pigmentation even lower than the control group not treated with any stimulant. Accordingly, it can be seen that the *Saururus chinensis* extract has superior pigmentation inhibiting effect and skin whitening effect.

Figure 38:
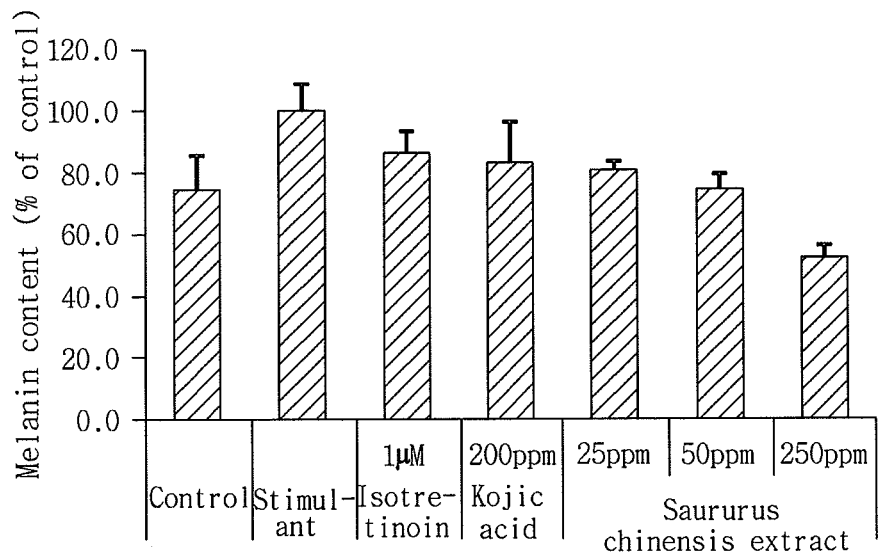
FIG. 38 shows acnegenic pigmentation inhibiting effect of a *Glycyrrhizae radix* extract.

The result for the *Glycyrrhizae radix* extract is shown in FIG. 38. Referring to FIG. 38, the *Glycyrrhizae radix* extract inhibits pigmentation in a concentration-dependent manner. Especially, at 250 ppm, the pigmentation inhibiting effect was very superior, with the degree of pigmentation even lower than the control group not treated with any stimulant. Accordingly, it can be seen that the *Glycyrrhizae radix* extract has very superior pigmentation inhibiting effect and skin whitening effect.

Figure 39:
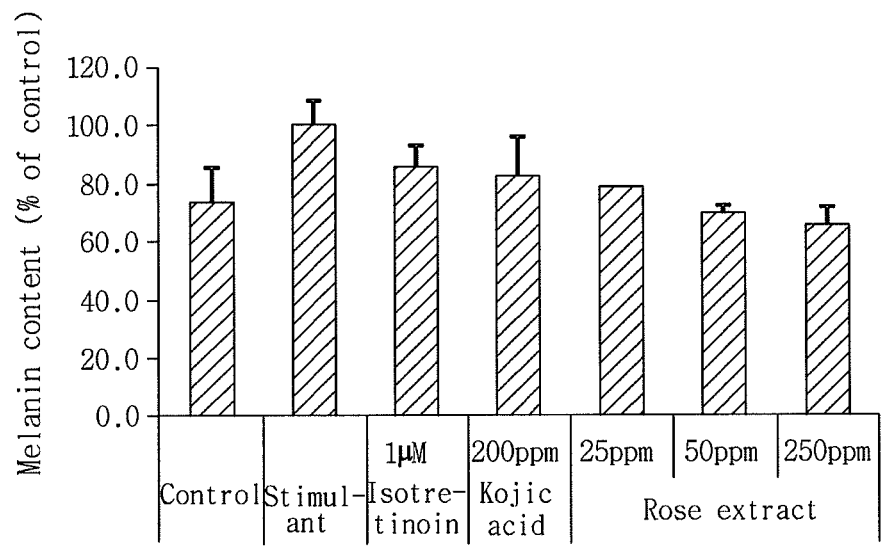
FIG. 39 shows acnegenic pigmentation inhibiting effect of a rose extract.

The result for the rose extract is shown in FIG. 39. Referring to FIG. 39, the rose extract inhibits pigmentation in a concentration-dependent manner. Especially, at 250 ppm, the pigmentation inhibiting effect was very superior, with the degree of pigmentation even lower than the control group not treated with any stimulant. Accordingly, it can be seen that the rose extract has very superior pigmentation inhibiting effect and skin whitening effect.

Figure 40:
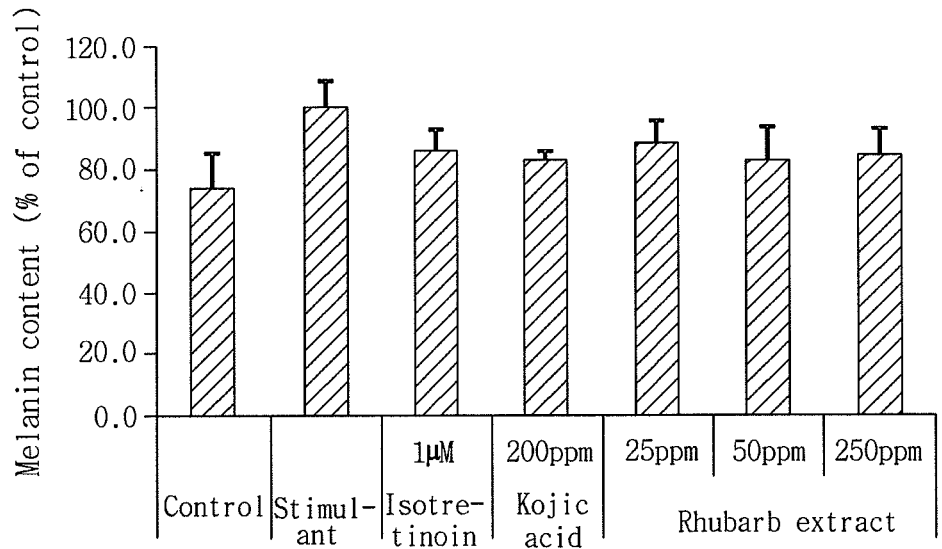
FIG. 40 shows acnegenic pigmentation inhibiting effect of a rhubarb extract.

The result for the rhubarb extract is shown in FIG. 40. Referring to FIG. 40, the rhubarb extract broadly inhibits pigmentation in a concentration-dependent manner. The pigmentation inhibiting effect was the highest at 50 ppm. Accordingly, it can be seen that the rhubarb extract has superior pigmentation inhibiting effect at relatively low concentration and is expected to have significant skin whitening effect.

Figure 41:
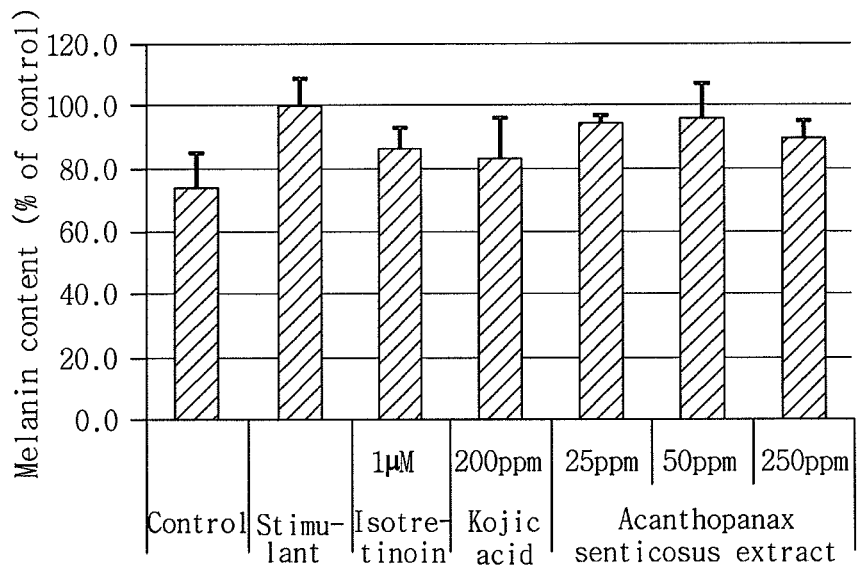
FIG. 41 shows acnegenic pigmentation inhibiting effect of an *Acanthopanax senticosus* extract.

The result for the *Acanthopanax senticosus* extract is shown in FIG. 41. Referring to FIG. 41, the *Acanthopanax senticosus* extract broadly inhibits pigmentation in a concentration-dependent manner. The pigmentation inhibiting effect was the highest at 250 ppm. Accordingly, it can be seen that the *Acanthopanax senticosus* extract has excellent pigmentation inhibiting effect and skin whitening effect.

Figure 42:
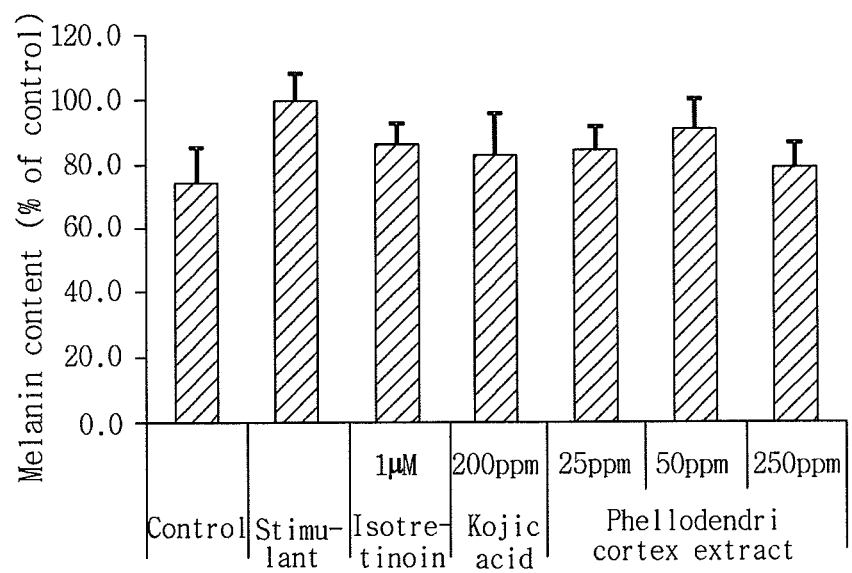
FIG. 42 shows acnegenic pigmentation inhibiting effect of a *Phellodendri* cortex extract.

And, the result for the *Phellodendri* cortex extract is shown in FIG. 42. Referring to FIG. 42, the *Phellodendri* cortex extract broadly inhibits pigmentation in a concentration-dependent manner. The pigmentation inhibiting effect was the highest at 250 ppm. Accordingly, it can be seen that the *Phellodendri* cortex extract has excellent pigmentation inhibiting effect and skin whitening effect.

Test Example 5

Inhibition of Acne Scars In Vitro

An in vitro acne scars model similar to the human acne environment was used to test the acne scar inhibiting effect of the *Astragalus membranaceus, Saururus chinensis* and *Glycyrrhizae radix* extracts. $6.0 \times 10^4$ golden hamster sebocytes were seeded on a 24-well culture plate. The cells were allowed to adhere to the bottom of the culture plate for one day. The culture medium was prepared by adding 10% fetal bovine serum (JRH Bioscience, Tokyo, Japan) to DMEM/Ham's F12 medium (1:1, Invitrogen, Carlsbad, Calif.) and then adding 100 mg/mL penicillin and 100 mg/mL streptomycin (both from Gibco, Milan, Italy).

After one day, the cells were treated with 50 µM linoleic acid, 50 µM arachidonic acid, 10 nM dihydrotestosterone, and 0.5% *Propionibacterium acnes* (*P. acnes*) as stimulants to induce inflammatory acne. At the same time, the cells were treated with *Astragalus membranaceus, Saururus chinensis* or *Glycyrrhizae radix* extract, and their acne scar inhibiting effect was investigated. DMSO was used as negative control, and 100 nM isotretinoin, which is a prescription drug used to treat acne, was used as positive control. One day after the treatment with the stimulants and the extracts, the degradation activity of gelatin of matrix metalloproteinase (MMP) which is dissolved to medium was measured by gelatin zymography.

Specifically, the procedure was as follows. 5 μL of the cell medium was mixed with 5 μL of tris-glycine sample buffer (Invitrogen, Carlsbad, Calif.) and subjected to electrophoresis on 10% acrylamide gel containing 2 mg/mL gelatin for 2 hours at 150 V. After separating the gel from a frame and reacting with a renaturing buffer for 30 minutes and then with a developing buffer for 30 minutes at room temperature, it was further incubated at 37° C. for 8 hours in a developing buffer. After removing the developing buffer and washing 3 times with PBS, the gel was stained with SimplyBlue (Invitrogen, Carlsbad, Calif.) for 1 hour. The stained gel was washed with distilled water until the band was sufficiently distinguished from the background and then observed.

Figure 43:
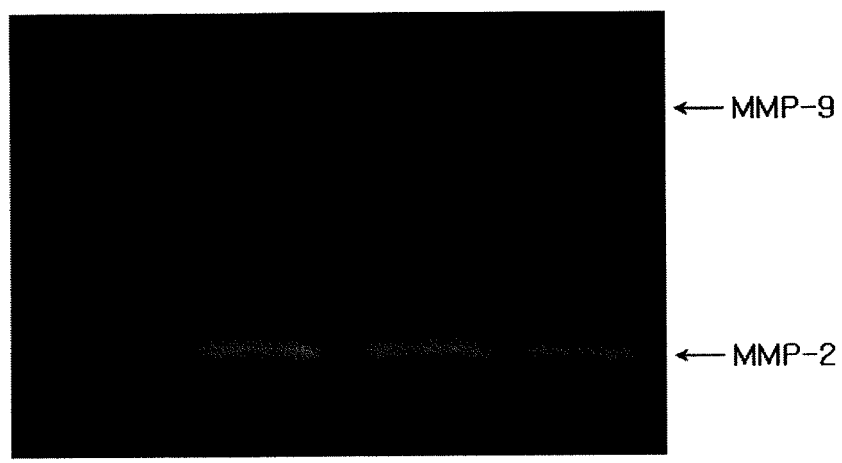
FIGS. 43-45 show acne scar inhibiting effect of an *Astragalus membranaceus* extract.
Figure 44:
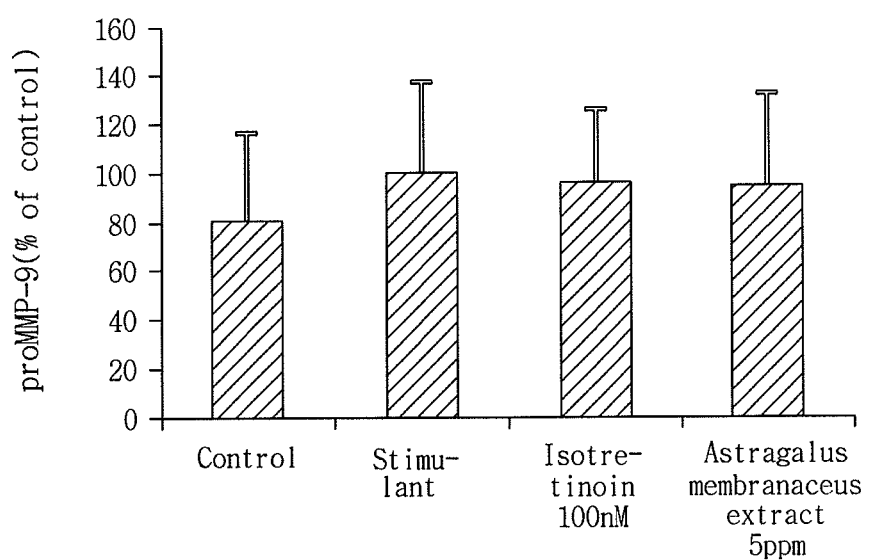
Figure 45:
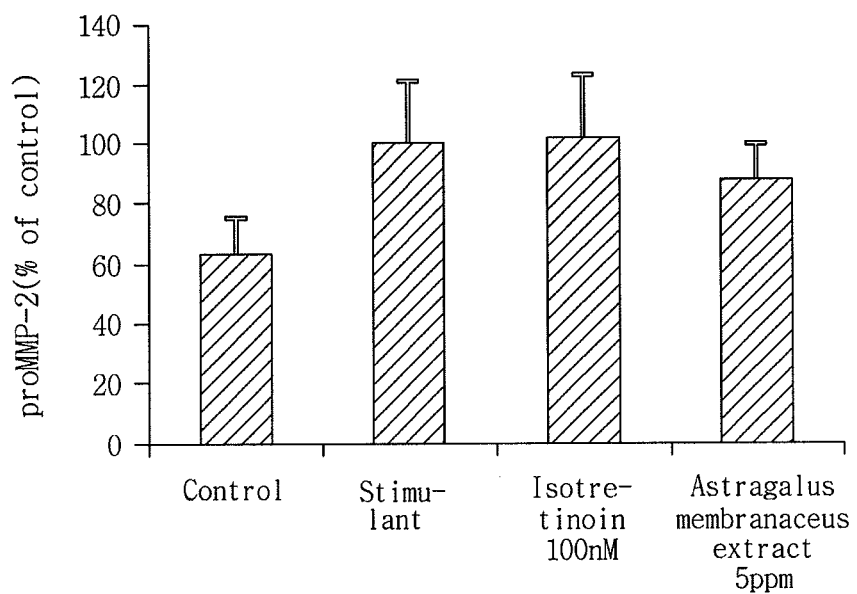

The result for the *Astragalus membranaceus* extract is shown in FIGS. 43-45. From FIG. 43, MMP-9 and MMP-2 separated by the electrophoresis can be identified. From FIG. 44, it can be seen that the *Astragalus membranaceus* extract has MMP-9 inhibiting effect. And, from FIG. 45, it can be seen that the *Astragalus membranaceus* extract has better MMP-2 inhibiting effect than isotretinoin, which is a prescription drug widely used to treat acne.

Figure 46:
FIGS. 46-48 show acne scar inhibiting effect of a *Saururus chinensis* extract.
Figure 47:
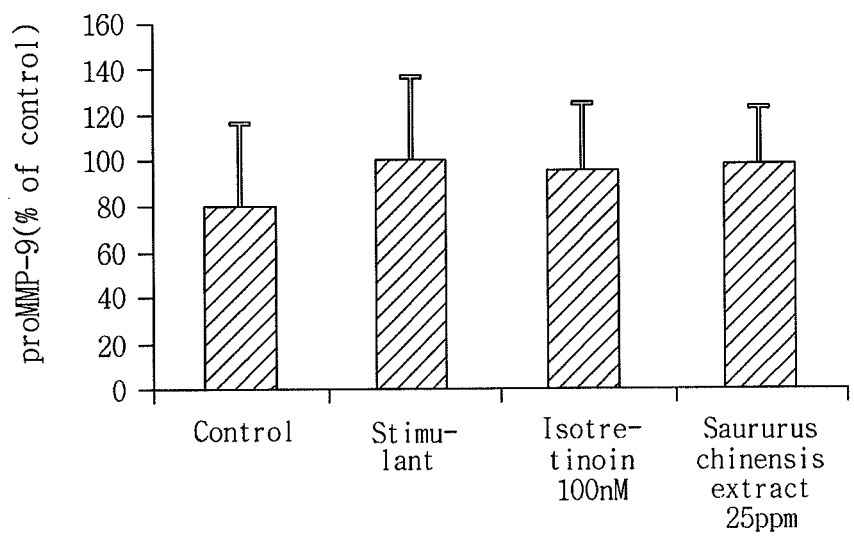
Figure 48:
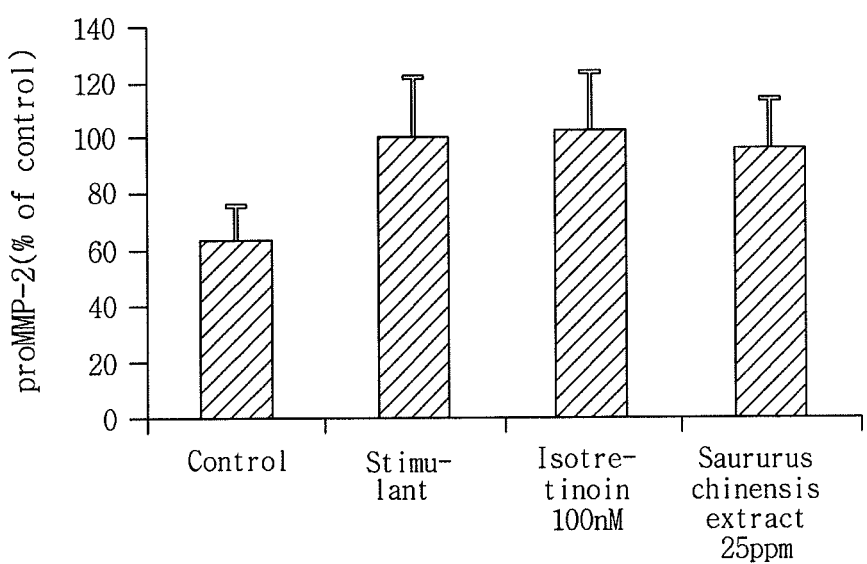

The result for the *Saururus chinensis* extract is shown in FIGS. 46-48. From FIG. 46, MMP-9 and MMP-2 separated by the electrophoresis can be identified. From FIGS. 47 and 48, it can be seen that the *Saururus chinensis* extract has MMP-9 and MMP-2 inhibiting effect. The inhibiting effect is comparable to that of isotretinoin, which is a prescription drug widely used to treat acne.

Figure 49:
FIGS. 49-51 show acne scar inhibiting effect of a *Glycyrrhizae radix* extract.
Figure 50:
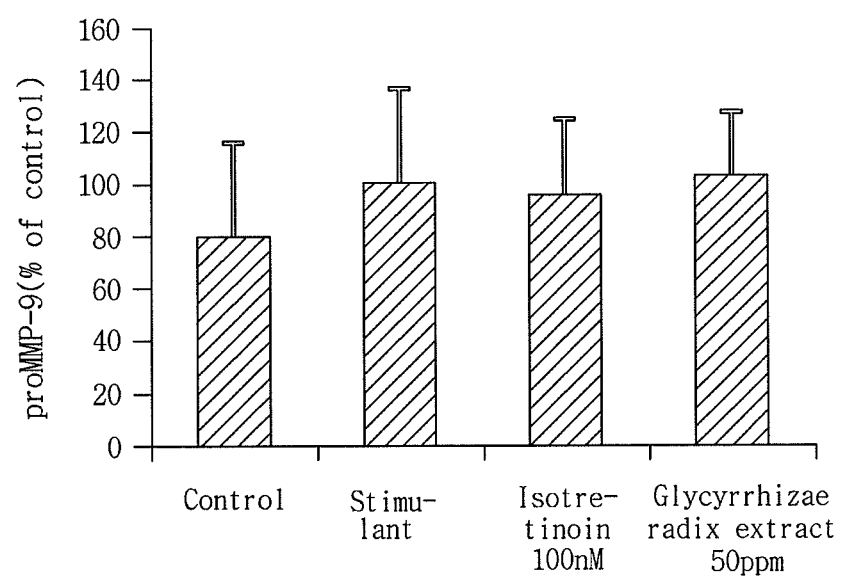
Figure 51:
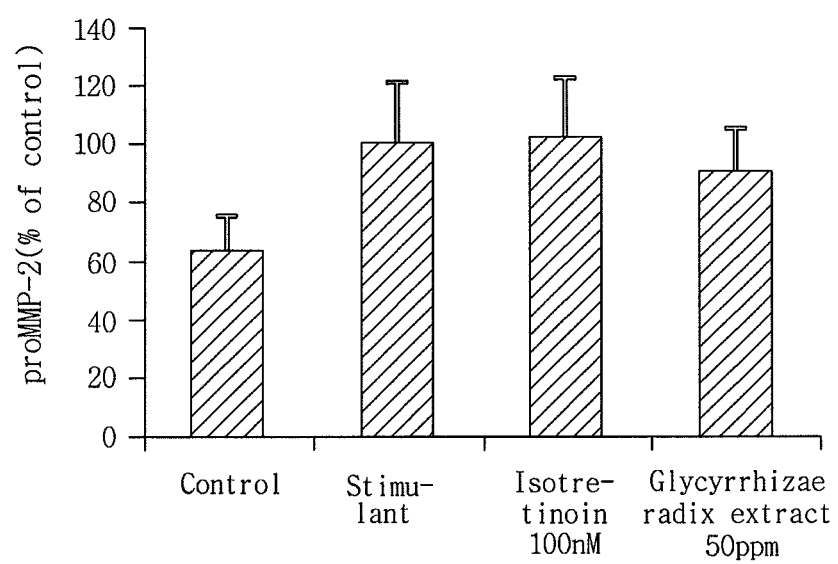

And, the result for the *Glycyrrhizae radix* extract is shown in FIGS. 49-51. From FIG. 49, MMP-9 and MMP-2 separated by the electrophoresis can be identified. From FIGS. 50 and 51 show the MMP-9 and MMP-2 inhibiting effect of the *Glycyrrhizae radix* extract. Especially, the *Glycyrrhizae radix* extract has superior MMP-2 inhibiting effect.

The following formulation examples of the composition are provided for illustrative purposes and are not intended to limit the present disclosure.

Formulation Example 1

Preparation of Soft Capsule

*Astragalus membranaceus, Saururus chinensis, Glycyrrhizae radix*, rose, rhubarb, *Acanthopanax senticosus* or *Phellodendri* cortex extract (80 mg), vitamin E (9 mg), vitamin C (9 mg), palm oil (2 mg), hydrogenated vegetable oil (8 mg), yellow beeswax (4 mg) and lecithin (9 mg) were mixed and prepared into a soft capsule filling solution according to the commonly employed method. 400 mg of the filling solution was filled per each capsule to prepare a soft capsule. Separately from this, a soft capsule sheet was prepared from gelatin (66 wt %), glycerin 24 (wt %) and sorbitol (10 wt %). Then, the filling solution was filled to prepare a soft capsule containing 400 mg of the composition according to the present disclosure.

Formulation Example 2

Preparation of Tablet

*Astragalus membranaceus, Saururus chinensis, Glycyrrhizae radix*, rose, rhubarb, *Acanthopanax senticosus* or *Phellodendri* cortex extract (80 mg), vitamin E (9 mg), vitamin C (9 mg), galactooligosaccharide (200 mg), lactose (60 mg) and maltose (140 mg) were mixed. After granulating using a fluidized-bed dryer, sugar ester (6 mg) was added. The resulting composition (504 mg) was prepared into a tablet according to the commonly employed method.

Formulation Example 3

Preparation of Drink

*Astragalus membranaceus, Saururus chinensis, Glycyrrhizae radix*, rose, rhubarb, *Acanthopanax senticosus* or *Phellodendri* cortex extract (80 mg), vitamin E (9 mg), vitamin C (9 mg), glucose (10 g), citric acid (0.6 g) and oligosaccharide syrup (25 g) were mixed. After adding purified water (300 mL), 200 mL of the resultant was filled in each bottle. Then, a drink was prepared by sterilizing at 130° C. for 4-5 seconds.

Formulation Example 4

Preparation of Granule

*Astragalus membranaceus, Saururus chinensis, Glycyrrhizae radix*, rose, rhubarb, *Acanthopanax senticosus* or *Phellodendri* cortex extract (80 mg), vitamin E (9 mg), vitamin C (9 mg), anhydrous crystalline glucose (250 mg) and starch (550 mg) were mixed, granulated using a fluidized-bed granulator, and filled in a pouch.

Formulation Example 5

Preparation of Soft Capsule

*Astragalus membranaceus* extract (40 mg), *Saururus chinensis* extract (40 mg), vitamin E (9 mg), vitamin C (9 mg), palm oil (2 mg), hydrogenated vegetable oil (8 mg), yellow beeswax (4 mg) and lecithin (9 mg) were mixed and prepared into a soft capsule filling solution according to the commonly employed method. 400 mg of the filling solution was filled per each capsule to prepare a soft capsule. Separately from this, a soft capsule sheet was prepared from gelatin (66 wt %), glycerin 24 (wt %) and sorbitol (10 wt %). Then, the filling solution was filled to prepare a soft capsule containing 400 mg of the composition according to the present disclosure.

Formulation Example 6

Preparation of Tablet

*Astragalus membranaceus, Saururus chinensis, Glycyrrhizae radix* and rose extracts (20 mg each) were mixed with vitamin E (9 mg), vitamin C (9 mg), galactooligosaccharide (200 mg), lactose (60 mg) and maltose (140 mg). After granulating using a fluidized-bed dryer, sugar ester (6 mg)

was added. The resulting composition (504 mg) was prepared into a tablet according to the commonly employed method.

Formulation Example 7

Preparation of Drink

*Astragalus membranaceus, Saururus chinensis* and *Glycyrrhizae radix* extracts (same weight) were mixed to prepare a mixture (80 mg). After mixing the mixture with vitamin E (9 mg), vitamin C (9 mg), glucose (10 g), citric acid (0.6 g) and oligosaccharide syrup (25 g) and adding purified water (300 mL), 200 mL of the resultant was filled in each bottle. Then, a drink was prepared by sterilizing at 130° C. for 4-5 seconds.

Formulation Example 8

Preparation of Granule

Rose, rhubarb, *Acanthopanax senticosus* and *Phellodendri* cortex extracts (20 mg each) were mixed with vitamin E (9 mg), vitamin C (9 mg), anhydrous crystalline glucose (250 mg) and starch (550 mg), granulated using a fluidized-bed granulator, and filled in a pouch.

Formulation Example 9

Preparation of Emollient Lotion (Skin Lotion)

*Astragalus membranaceus, Saururus chinensis, Glycyrrhizae radix*, rose, rhubarb, *Acanthopanax senticosus* or *Phellodendri* cortex extract (0.3 mg), butylene glycol (6.0 mg), propylene glycol (6.0 mg), carboxyvinyl polymer (0.3 mg), PEG-12 nonyl phenyl ether (0.6 mg), Polysorbate 80 (1.2 mg), ethanol (30.0 mg), triethanolamine (0.3 mg) and purified water (255 mg) were mixed with preservative, pigment and fragrance (small quantities) and prepared into an emollient lotion according to the commonly employed method by adding each component in the above amounts and mixing uniformly.

Formulation Example 10

Preparation of Nourishing Lotion (Milk Lotion)

*Astragalus membranaceus, Saururus chinensis, Glycyrrhizae radix*, rose, rhubarb, *Acanthopanax senticosus* or *Phellodendri* cortex extract (0.3 mg), beeswax (12.0 mg), Polysorbate 60 (4.5 mg), sorbitan sesquiolate (4.5 mg), liquid paraffin (1.5 mg), Montana 202 (Seppic, 15 mg), glycerin (9.0 mg), butylene glycol (9.0 mg), propylene glycol (9.0 mg), carboxyvinyl polymer (0.3 mg), triethanolamine (0.6 mg) and purified water (234 mg) were mixed with preservative, pigment and fragrance (small quantities) and prepared into a nourishing lotion according to the commonly employed method by adding each component in the above amounts and mixing uniformly.

Formulation Example 11

Preparation of Massage Cream

*Astragalus membranaceus, Saururus chinensis, Glycyrrhizae radix*, rose, rhubarb, *Acanthopanax senticosus* or *Phellodendri* cortex extract (0.3 mg), beeswax (30.0 mg), Polysorbate 60 (4.5 mg), PEG 60 hydrogenated castor oil (6.0 mg), sorbitan sesquiolate (2.4 mg), liquid paraffin (120.0 mg), squalane (15.0 mg), Montana 202 (Seppic, 12.0 mg), glycerin (15.0 mg), butylene glycol (12.0 mg), propylene glycol (12.0 mg), triethanolamine (0.6 mg) and purified water (70 mg) were mixed with preservative, pigment and fragrance (small quantities) and prepared into a massage cream according to the commonly employed method by adding each component in the above amounts and mixing uniformly.

Formulation Example 12

Preparation of Pack

*Astragalus membranaceus, Saururus chinensis, Glycyrrhizae radix*, rose, rhubarb, *Acanthopanax senticosus* or *Phellodendri* cortex extract (0.5 mg), beta-1,3-glucan (1.0 mg), polyvinyl alcohol (13.0 mg), sodium carboxymethyl cellulose (0.2 mg), glycerin (5.0 mg), allantoin (0.1 mg), ethanol (6.0 mg), PEG-12 nonyl phenyl ether (0.3 mg) and Polysorbate 60 (0.3 mg) were mixed with preservative, pigment and fragrance (small quantities). After adding purified water, the mixture was prepared into a pack according to the commonly employed method by adding each component in the above amounts and mixing uniformly.

Formulation Example 13

Preparation of Gel

*Astragalus membranaceus, Saururus chinensis, Glycyrrhizae radix*, rose, rhubarb, *Acanthopanax senticosus* or *Phellodendri* cortex extract (0.05 mg), beta-1,3-glucan (0.1 mg), sodium ethylenediamine acetate (0.05 mg), glycerin (5.0 mg), carboxyvinyl polymer (0.3 mg), ethanol (5.0 mg), PEG-60 hydrogenated castor oil (0.5 mg) and triethanolamine (0.3 mg) were mixed with preservative, pigment and fragrance (small quantities). After adding purified water, the mixture was prepared into a gel according to the commonly employed method by adding each component in the above amounts and mixing uniformly.

Formulation Example 14

Preparation of Emollient Lotion (Skin Lotion)

*Astragalus membranaceus, Saururus chinensis* and *Glycyrrhizae radix* extracts (0.1 mg each), butylene glycol (6.0 mg), propylene glycol (6.0 mg), carboxyvinyl polymer (0.3 mg), PEG-12 nonyl phenyl ether (0.6 mg), Polysorbate 80 (1.2 mg), ethanol (30.0 mg), triethanolamine (0.3 mg) and purified water (255 mg) were mixed with preservative, pigment and fragrance (small quantities) and prepared into an emollient lotion according to the commonly employed method by adding each component in the above amounts and mixing uniformly.

Formulation Example 15

Preparation of Nourishing Lotion (Milk Lotion)

*Astragalus membranaceus* and *Saururus chinensis* extracts (0.15 mg each), beeswax (12.0 mg), Polysorbate 60 (4.5 mg), sorbitan sesquiolate (4.5 mg), liquid paraffin (1.5 mg), Montana 202 (Seppic, 15 mg), glycerin (9.0 mg), butylene glycol (9.0 mg), propylene glycol (9.0 mg), carboxyvinyl polymer (0.3 mg), triethanolamine (0.6 mg) and purified water (234 mg) were mixed with preservative, pigment and fragrance (small quantities) and prepared into a nourishing lotion according to the commonly employed method by adding each component in the above amounts and mixing uniformly.

Formulation Example 16

Preparation of Massage Cream

Rose, rhubarb, *Acanthopanax senticosus* and *Phellodendri* cortex extracts (0.075 mg each), beeswax (30.0 mg), Polysorbate 60 (4.5 mg), PEG 60 hydrogenated castor oil (6.0 mg), sorbitan sesquiolate (2.4 mg), liquid paraffin (120.0 mg), squalane (15.0 mg), Montana 202 (Seppic, 12.0 mg), glycerin (15.0 mg), butylene glycol (12.0 mg), propylene glycol (12.0 mg), triethanolamine (0.6 mg) and purified water (70 mg) were mixed with preservative, pigment and fragrance (small quantities) and prepared into a massage cream according to the commonly employed method by adding each component in the above amounts and mixing uniformly.

Formulation Example 17

Preparation of Pack

*Acanthopanax senticosus* and *Phellodendri* cortex extracts (0.25 mg each), beta-1,3-glucan (1.0 mg), polyvinyl alcohol (13.0 mg), sodium carboxymethyl cellulose (0.2 mg), glycerin (5.0 mg), allantoin (0.1 mg), ethanol (6.0 mg), PEG-12 nonyl phenyl ether (0.3 mg) and Polysorbate 60 (0.3 mg) were mixed with preservative, pigment and fragrance (small quantities). After adding purified water, the mixture was prepared into a pack according to the commonly employed method by adding each component in the above amounts and mixing uniformly.

Formulation Example 18

Preparation of Gel

*Astragalus membranaceus, Saururus chinensis, Glycyrrhizae radix*, rose and rhubarb extracts (0.01 mg each), beta-1,3-glucan (0.1 mg), sodium ethylenediamine acetate (0.05 mg), glycerin (5.0 mg), carboxyvinyl polymer (0.3 mg), ethanol (5.0 mg), PEG-60 hydrogenated castor oil (0.5 mg) and triethanolamine (0.3 mg) were mixed with preservative, pigment and fragrance (small quantities). After adding purified water, the mixture was prepared into a gel according to the commonly employed method by adding each component in the above amounts and mixing uniformly.

Formulation Example 19

Preparation of Ointment for External Skin Application

*Astragalus membranaceus, Saururus chinensis, Glycyrrhizae radix*, rose, rhubarb, *Acanthopanax senticosus* or *Phellodendri* cortex extract (2.0 mg), beta-1,3-glucan (10.0 mg), beeswax (10.0 mg), Polysorbate 60 (5.0 mg), PEG 60 hydrogenated castor oil (2.0 mg), sorbitan sesquiolate (0.5 mg), vaseline (5.0 mg), liquid paraffin (10.0 mg), squalane (5.0 mg), shea butter (3.0 mg), caprylic/capric triglyceride (5.0 mg), glycerin (10 mg), propylene glycol (10.2 mg) and triethanolamine (0.2 mg) were mixed with preservative, pigment and fragrance (small quantities). After adding purified water, the mixture was prepared into an ointment according to the commonly employed method by adding each component in the above amounts and mixing uniformly.

Formulation Example 20

Preparation of Patch for Topical Application

*Astragalus membranaceus, Saururus chinensis, Glycyrrhizae radix*, rose, rhubarb, *Acanthopanax senticosus* or *Phellodendri* cortex extract (1.0 mg), beta-1,3-glucan (3.0 mg), hexylene glycol (20.0 mg), diethylamine (0.7 mg), polyacrylic acid (Carbopol 934P, 1.0 mg), sodium sulfite (0.1 mg), polyoxyethylene lauryl ether (E.O=9, 1.0 mg), polyhydroxyethylene cetyl stearyl ether (Cetomacrogol 1000, 1.0 mg), viscous paraffin oil (2.5 mg), caprylic/capric ester (Cetiol LC, 2.5 mg) and PEG 400 (3.0 mg) were mixed with preservative, pigment and fragrance (small quantities). After adding purified water, the mixture was prepared into a patch according to the commonly employed method by adding each component in the above amounts and mixing uniformly.

Formulation Example 21

Preparation of Ointment for External Skin Application

*Astragalus membranaceus* and *Saururus chinensis* extracts (1.0 mg each), beta-1,3-glucan (10.0 mg), beeswax (10.0 mg), Polysorbate 60 (5.0 mg), PEG 60 hydrogenated castor oil (2.0 mg), sorbitan sesquiolate (0.5 mg), vaseline (5.0 mg), liquid paraffin (10.0 mg), squalane (5.0 mg), shea butter (3.0 mg), caprylic/capric triglyceride (5.0 mg), glycerin (10 mg), propylene glycol (10.2 mg) and triethanolamine (0.2 mg) were mixed with preservative, pigment and fragrance (small quantities). After adding purified water, the mixture was prepared into an ointment according to the commonly employed method by adding each component in the above amounts and mixing uniformly.

Formulation Example 22

Preparation of Patch for Topical Application

Rose, rhubarb, *Acanthopanax senticosus* and *Phellodendri* cortex extracts (0.25 mg each), beta-1,3-glucan (3.0 mg), hexylene glycol (20.0 mg), diethylamine (0.7 mg), polyacrylic acid (Carbopol 934P, 1.0 mg), sodium sulfite (0.1 mg), polyoxyethylene lauryl ether (E.O=9, 1.0 mg), polyhydroxyethylene cetyl stearyl ether (Cetomacrogol 1000, 1.0 mg), viscous paraffin oil (2.5 mg), caprylic/capric ester (Cetiol LC, 2.5 mg) and PEG 400 (3.0 mg) were mixed with preservative, pigment and fragrance (small quantities). After adding purified water, the mixture was prepared into a patch according to the commonly employed method by adding each component in the above amounts and mixing uniformly.

While the present disclosure has been described with respect to the specific embodiments, it will be apparent to those skilled in the art that various changes and modifications may be made without departing from the spirit and scope of the disclosure as defined in the following claims.

INDUSTRIAL APPLICABILITY

The composition according to the present disclosure is efficacious in suppressing acnegenic pigmentation and/or pitted scars, and can be used to advantage in various ways in the fields of cosmetics, foods and drugs.

We claim:

1. A method for suppressing acne scars comprising administering an effective amount of a composition comprising one or more extracts selected from the group consisting of *Astragalus membranaceus* and *Saururus chinensis* to a subject in need thereof, wherein the one or more extracts suppresses gelatinase.

2. The method according to claim 1, wherein the composition further comprises an extract of *Glycyrrhizae radix*.

3. The method according to claim 2, wherein one or more extracts selected from the group consisting of *Astragalus membranaceus, Saururus chinensis*, and *Glycyrrhizae radix* is present in the composition in an amount of 0.1-20 wt % based on the total weight of the composition.

4. The method according to claim 1, wherein the composition is a composition for external skin application.

5. The method according to claim 1, wherein the composition is a cosmetic composition.

6. The method according to claim 1, wherein the composition is a pharmaceutical composition.

7. The method according to claim 1, wherein the composition is a food additive or health food composition.

* * * * *